US009099939B2

(12) United States Patent
Jungnickel et al.

(10) Patent No.: US 9,099,939 B2
(45) Date of Patent: Aug. 4, 2015

(54) LINEAR ELECTRO-POLYMER MOTORS AND DEVICES HAVING THE SAME

(75) Inventors: Uwe Jungnickel, Koenigstein (DE); Benedikt Heil, Ober-Morlen (DE)

(73) Assignee: BRAUN GMBH, Kronberg (DE)

( * ) Notice: Subject to any disclaimer, the term of this patent is extended or adjusted under 35 U.S.C. 154(b) by 281 days.

(21) Appl. No.: 13/557,245

(22) Filed: Jul. 25, 2012

(65) Prior Publication Data

US 2013/0025079 A1     Jan. 31, 2013

Related U.S. Application Data

(60) Provisional application No. 61/511,154, filed on Jul. 25, 2011.

(51) Int. Cl.
    *H02N 2/04*         (2006.01)
    *H02N 2/02*         (2006.01)
    *A61C 17/34*        (2006.01)
    *B26B 19/28*        (2006.01)

(52) U.S. Cl.
CPC ............ *H02N 2/02* (2013.01); *A61C 17/3436* (2013.01); *A61C 17/3445* (2013.01); *B26B 19/282* (2013.01); *H02N 2/046* (2013.01)

(58) Field of Classification Search
CPC ........... H02N 2/02; H02N 2/026; H02N 2/04; H02N 2/046
USPC ................................................ 310/328, 800
See application file for complete search history.

(56) References Cited

U.S. PATENT DOCUMENTS

| 2,798,241 | A | 7/1957 | Cohen |
| 3,109,619 | A | 11/1963 | Krug et al. |
| 3,220,039 | A | 11/1965 | Dayton et al. |
| 3,417,417 | A | 12/1968 | Rhodes |
| 3,461,874 | A | 8/1969 | Martinez |
| 3,496,500 | A | 2/1970 | Romary |
| 3,571,544 | A | 3/1971 | Sheehan |
| 3,782,799 | A | 1/1974 | Hansen |
| 3,796,850 | A | 3/1974 | Moreland, II et al. |
| 3,802,420 | A | 4/1974 | Moffat et al. |
| 3,810,147 | A | 5/1974 | Lichtblau |
| 3,904,841 | A | 9/1975 | Swatman |
| 4,156,620 | A | 5/1979 | Clemens |

(Continued)

FOREIGN PATENT DOCUMENTS

| AU | 2005100387 A4 | 5/2005 |
| CH | 688 537 A5 | 11/1997 |

(Continued)

OTHER PUBLICATIONS

U.S. Appl. No. 13/557,243, filed Jul. 25, 2012, Utsch et al.

(Continued)

*Primary Examiner* — Derek Rosenau
(74) *Attorney, Agent, or Firm* — Vladimir Vitenberg

(57) ABSTRACT

A linear electro-polymer motor includes a fixed member, a linear shaft having an axis, a polymer actuator, and a bias member. The polymer actuator includes a first end fixedly connected to the linear shaft and a second end fixedly connected to the fixed member. The bias member includes a first end fixedly connected to the linear shaft and a second end fixedly connected to the fixed member. The polymer actuator changes length after receipt of voltage to linearly move the linear shaft along the axis.

15 Claims, 14 Drawing Sheets

(56) References Cited

U.S. PATENT DOCUMENTS

| | | |
|---|---|---|
| 4,274,070 A | 6/1981 | Thiene |
| 4,333,197 A | 6/1982 | Kuris |
| 4,349,814 A | 9/1982 | Akehurst |
| 4,352,098 A | 9/1982 | Stephen et al. |
| 4,365,376 A | 12/1982 | Oda et al. |
| 4,371,118 A | 2/1983 | Sontheimer et al. |
| 4,374,354 A | 2/1983 | Petrovic et al. |
| 4,413,199 A | 11/1983 | Fischer |
| 4,420,851 A | 12/1983 | Wiener |
| 4,492,574 A | 1/1985 | Warrin et al. |
| 4,502,497 A | 3/1985 | Siahou |
| 4,506,400 A | 3/1985 | Klein |
| 4,514,172 A | 4/1985 | Behringer |
| 4,523,083 A | 6/1985 | Hamilton |
| 4,546,266 A | 10/1985 | Zenick et al. |
| 4,595,849 A | 6/1986 | Cuenoud |
| 4,595,850 A | 6/1986 | Woog |
| 4,603,448 A | 8/1986 | Middleton et al. |
| 4,682,584 A | 7/1987 | Pose |
| 4,698,869 A | 10/1987 | Mierau et al. |
| 4,704,602 A | 11/1987 | Asbrink |
| 4,716,614 A | 1/1988 | Jones et al. |
| 4,736,207 A | 4/1988 | Siikaria et al. |
| 4,820,152 A | 4/1989 | Warrin et al. |
| 4,827,550 A | 5/1989 | Graham et al. |
| 4,845,796 A | 7/1989 | Mosley |
| 4,878,679 A | 11/1989 | Plank et al. |
| 4,900,252 A | 2/1990 | Liefke et al. |
| 4,910,634 A | 3/1990 | Pipkorn |
| 4,914,376 A | 4/1990 | Meyer |
| 5,014,794 A | 5/1991 | Hansson |
| 5,065,137 A | 11/1991 | Herman |
| 5,072,164 A | 12/1991 | Prius et al. |
| 5,099,536 A | 3/1992 | Hirabayashi |
| 5,165,131 A | 11/1992 | Staar |
| 5,168,186 A | 12/1992 | Yashiro |
| 5,184,959 A | 2/1993 | Oryhon et al. |
| 5,189,751 A | 3/1993 | Giuliani |
| 5,217,478 A | 6/1993 | Rexroth |
| 5,233,323 A | 8/1993 | Burkett et al. |
| 5,259,083 A | 11/1993 | Stansbury, Jr. |
| 5,263,218 A | 11/1993 | Giuliani et al. |
| 5,269,794 A | 12/1993 | Rexroth |
| 5,274,735 A | 12/1993 | Okada |
| 5,289,604 A | 3/1994 | Kressner |
| 5,305,492 A | 4/1994 | Giuliani et al. |
| 5,309,590 A | 5/1994 | Giuliani et al. |
| 5,337,435 A | 8/1994 | Krasner et al. |
| 5,341,534 A | 8/1994 | Serbinski et al. |
| 5,355,544 A | 10/1994 | Dirksing |
| 5,367,599 A | 11/1994 | Okada |
| 5,378,153 A | 1/1995 | Giuliani et al. |
| 5,381,576 A | 1/1995 | Hwang |
| 5,392,028 A | 2/1995 | Pichl |
| 5,404,608 A | 4/1995 | Hommann |
| 5,448,792 A | 9/1995 | Wiedemann et al. |
| 5,476,384 A | 12/1995 | Giuliani et al. |
| 5,502,861 A | 4/1996 | Spieler et al. |
| 5,504,959 A | 4/1996 | Yukawa et al. |
| 5,524,312 A | 6/1996 | Tan et al. |
| 5,544,382 A | 8/1996 | Giuliani et al. |
| 5,561,881 A | 10/1996 | Klinger et al. |
| 5,576,693 A | 11/1996 | Tyren et al. |
| 5,577,285 A | 11/1996 | Drossler |
| 5,613,259 A | 3/1997 | Craft et al. |
| 5,617,503 A | 4/1997 | Fronen et al. |
| 5,617,601 A | 4/1997 | McDougall |
| 5,673,451 A | 10/1997 | Moore et al. |
| 5,693,042 A | 12/1997 | Boiarski et al. |
| 5,700,146 A | 12/1997 | Kucar |
| 5,732,432 A | 3/1998 | Hui |
| 5,749,885 A | 5/1998 | Sjostrom et al. |
| 5,760,580 A | 6/1998 | Tyren |
| 5,781,955 A | 7/1998 | Hendricks |
| 5,784,742 A | 7/1998 | Giuliani et al. |
| 5,799,356 A | 9/1998 | Kawashima |
| 5,812,065 A | 9/1998 | Schrott et al. |
| 5,815,872 A | 10/1998 | Meginniss, III et al. |
| 5,836,030 A | 11/1998 | Hazeu et al. |
| 5,864,288 A | 1/1999 | Hogan |
| 5,888,031 A | 3/1999 | Buck et al. |
| 5,897,315 A | 4/1999 | Nakayama et al. |
| 5,934,908 A | 8/1999 | Woog et al. |
| 5,939,983 A | 8/1999 | Rudell et al. |
| 5,943,723 A | 8/1999 | Hilfinger et al. |
| 5,955,799 A | 9/1999 | Amaya et al. |
| 5,974,615 A | 11/1999 | Schwarz-Hartmann et al. |
| 5,994,855 A | 11/1999 | Lundell et al. |
| 5,998,965 A | 12/1999 | Carlucci et al. |
| 6,017,354 A | 1/2000 | Culp et al. |
| 6,021,538 A | 2/2000 | Kressner et al. |
| 6,029,303 A | 2/2000 | Dewan |
| 6,043,646 A | 3/2000 | Jansseune |
| 6,098,288 A | 8/2000 | Miyagawa et al. |
| 6,133,701 A | 10/2000 | Gokturk et al. |
| 6,140,723 A | 10/2000 | Matsui et al. |
| 6,140,802 A | 10/2000 | Lundell et al. |
| 6,163,258 A | 12/2000 | Rudell et al. |
| 6,177,870 B1 | 1/2001 | Lian et al. |
| 6,193,510 B1 | 2/2001 | Tsimerman |
| 6,195,828 B1 | 3/2001 | Fritsch |
| 6,202,242 B1 | 3/2001 | Salmon et al. |
| 6,212,052 B1 | 4/2001 | Heuer et al. |
| 6,227,853 B1 | 5/2001 | Hansen et al. |
| 6,234,051 B1 | 5/2001 | Bareggi |
| 6,265,789 B1 | 7/2001 | Honda et al. |
| 6,322,573 B1 | 11/2001 | Muryama |
| 6,326,884 B1 | 12/2001 | Wohlrabe |
| 6,353,956 B1 | 3/2002 | Berge |
| 6,359,559 B1 | 3/2002 | Rudell et al. |
| 6,367,108 B1 | 4/2002 | Fritsch et al. |
| 6,389,633 B1 | 5/2002 | Rosen |
| 6,422,566 B1 | 7/2002 | Rudell et al. |
| 6,441,571 B1 | 8/2002 | Ibuki et al. |
| 6,446,294 B1 | 9/2002 | Specht |
| 6,453,497 B1 | 9/2002 | Chiang et al. |
| 6,498,456 B2 | 12/2002 | Ettes et al. |
| 6,517,348 B1 | 2/2003 | Ram |
| 6,531,873 B1 | 3/2003 | Wohlrabe |
| 6,536,068 B1 | 3/2003 | Yang et al. |
| 6,538,402 B2 | 3/2003 | Gokturk et al. |
| 6,545,576 B1 | 4/2003 | Marchini et al. |
| 6,590,763 B2 | 7/2003 | Kishimoto |
| 6,611,780 B2 | 8/2003 | Lundell et al. |
| 6,623,698 B2 | 9/2003 | Keo |
| 6,636,135 B1 | 10/2003 | Vetter |
| 6,648,641 B1 | 11/2003 | Viltro et al. |
| 6,716,028 B2 | 4/2004 | Rahman et al. |
| 6,731,213 B1 | 5/2004 | Smith |
| 6,734,795 B2 | 5/2004 | Price |
| 6,735,802 B1 | 5/2004 | Lundell et al. |
| 6,750,747 B2 | 6/2004 | Mandell et al. |
| 6,754,928 B2 | 6/2004 | Rosen |
| 6,760,945 B2 | 7/2004 | Ferber et al. |
| 6,766,824 B2 | 7/2004 | Taylor |
| 6,798,167 B1 | 7/2004 | Stratmann et al. |
| 6,792,640 B2 | 9/2004 | Levy et al. |
| 6,811,399 B2 | 11/2004 | Rahman et al. |
| 6,813,793 B2 | 11/2004 | Eliav |
| 6,845,537 B2 | 1/2005 | Wong |
| 6,850,167 B2 | 2/2005 | Rosen |
| 6,859,968 B2 | 3/2005 | Miller et al. |
| 6,868,919 B1 | 3/2005 | Manschitz et al. |
| 6,873,067 B2 | 3/2005 | Ichii et al. |
| 6,889,401 B2 | 5/2005 | Fattori et al. |
| 6,891,287 B2 | 5/2005 | Moret |
| 6,895,630 B2 | 5/2005 | Tini |
| 6,899,538 B2 | 5/2005 | Matoba |
| 6,918,300 B2 | 7/2005 | Grez et al. |
| 6,952,855 B2 | 10/2005 | Lev et al. |
| 6,954,961 B2 | 10/2005 | Ferber et al. |
| 6,958,553 B2 | 10/2005 | Ichii et al. |
| 6,964,076 B2 | 11/2005 | Zhuan |
| 6,966,093 B2 | 11/2005 | Eliav et al. |

(56) References Cited

U.S. PATENT DOCUMENTS

| | | |
|---|---|---|
| 6,973,694 B2 | 12/2005 | Schutz et al. |
| 7,011,520 B2 | 3/2006 | Rahman et al. |
| 7,024,717 B2 | 4/2006 | Hilscher et al. |
| 7,067,945 B2 | 6/2006 | Grez et al. |
| 7,086,111 B2 | 8/2006 | Hilscher et al. |
| 7,117,555 B2 | 10/2006 | Fattori et al. |
| 7,120,960 B2 | 10/2006 | Hilscher et al. |
| 7,140,058 B2 | 11/2006 | Gatzemeyer et al. |
| 7,174,972 B2 | 2/2007 | Kristen et al. |
| 7,194,862 B2 | 3/2007 | Sattinger |
| 7,207,080 B2 | 4/2007 | Hilscher et al. |
| 7,248,892 B2 | 7/2007 | White et al. |
| 7,258,546 B2 | 8/2007 | Beier et al. |
| 7,258,747 B2 | 8/2007 | Vago et al. |
| 7,288,863 B2 | 10/2007 | Kraus |
| 7,307,397 B2 | 12/2007 | Izumi et al. |
| 7,313,422 B2 | 12/2007 | White et al. |
| 7,315,098 B2 | 1/2008 | Kunita et al. |
| 7,334,283 B2 | 2/2008 | Kunita et al. |
| 7,373,170 B2 | 5/2008 | White et al. |
| 7,376,439 B2 | 5/2008 | White et al. |
| 7,386,904 B2 | 6/2008 | Fattori |
| 7,392,059 B2 | 6/2008 | White et al. |
| 7,409,741 B2 | 8/2008 | Dworzan |
| 7,411,511 B2 | 8/2008 | Kennish et al. |
| 7,422,582 B2 | 9/2008 | Malackowski et al. |
| 7,430,776 B2 | 10/2008 | Eliav |
| 7,431,682 B2 | 10/2008 | Zeiler et al. |
| 7,443,058 B2 | 10/2008 | Shimizu et al. |
| 7,443,059 B2 | 10/2008 | Kobayashi et al. |
| 7,448,108 B2 | 11/2008 | Gatzemeyer et al. |
| 7,469,703 B2 | 12/2008 | France et al. |
| 7,474,018 B2 | 1/2009 | Shimizu et al. |
| 7,474,065 B2 | 1/2009 | Kraus |
| 7,493,669 B2 | 2/2009 | Miller et al. |
| 7,495,358 B2 | 2/2009 | Kobayashi et al. |
| 7,520,016 B2 | 4/2009 | Kressner |
| 7,521,840 B2 | 4/2009 | Heim |
| 7,535,135 B2 | 5/2009 | Kardeis et al. |
| 7,552,497 B2 | 6/2009 | Gatzemeyer et al. |
| 7,562,121 B2 | 7/2009 | Berisford et al. |
| 7,621,015 B2 | 11/2009 | Hilscher et al. |
| 7,624,467 B2 | 12/2009 | Hilscher et al. |
| 7,627,922 B2 | 12/2009 | Miller et al. |
| 7,636,976 B2 | 12/2009 | Banning |
| 7,646,117 B2 | 1/2010 | Shimizu et al. |
| 7,654,271 B2 | 2/2010 | Wyatt et al. |
| 7,661,172 B2 | 2/2010 | Hilscher et al. |
| 7,673,360 B2 | 3/2010 | Hilscher et al. |
| 7,676,875 B2 | 3/2010 | Cho |
| 7,687,944 B2 | 3/2010 | Benning et al. |
| 7,698,771 B2 | 4/2010 | Gall |
| 7,712,174 B2 | 5/2010 | Shimizu et al. |
| 7,750,532 B2 | 7/2010 | Heim |
| 7,770,251 B2 | 8/2010 | Hilscher et al. |
| 7,774,886 B2 | 8/2010 | Hilscher et al. |
| 7,784,136 B2 | 8/2010 | Gatzemeyer et al. |
| 7,784,144 B2 | 8/2010 | Renault |
| 7,810,199 B2 | 10/2010 | Kressner |
| 7,827,644 B2 | 11/2010 | Eliav |
| 7,845,039 B2 | 12/2010 | Chan et al. |
| 7,849,549 B2 | 12/2010 | Hegemann et al. |
| 7,861,348 B2 | 1/2011 | Chan |
| 7,861,349 B2 | 1/2011 | Hilscher et al. |
| 7,876,003 B2 | 1/2011 | Bax |
| 7,877,832 B2 | 2/2011 | Reinbold |
| 7,887,559 B2 | 2/2011 | Deng et al. |
| 7,979,938 B2 | 7/2011 | Lilley et al. |
| 7,979,939 B2 | 7/2011 | Hilscher et al. |
| 8,015,648 B2 | 9/2011 | Hall |
| 8,020,238 B2 | 9/2011 | Eliav et al. |
| 8,021,065 B2 | 9/2011 | Lou |
| 8,032,964 B2 | 10/2011 | Farrell et al. |
| 8,032,965 B2 | 10/2011 | Asada et al. |
| 8,035,487 B2 | 10/2011 | Malackowski |
| 8,089,227 B2 | 1/2012 | Baertschi et al. |
| 8,143,817 B2 | 3/2012 | Izumi et al. |
| 8,181,301 B2 | 5/2012 | Hilscher et al. |
| 8,185,991 B2 | 5/2012 | Kressner |
| 8,218,711 B2 | 7/2012 | Neyer |
| 8,264,105 B2 | 9/2012 | Bax |
| 8,288,970 B2 | 10/2012 | Miller et al. |
| 8,314,586 B2 | 11/2012 | Lambantobing et al. |
| 8,317,424 B2 | 11/2012 | Chenvainu et al. |
| 8,336,155 B2 | 12/2012 | Crossman et al. |
| 8,341,791 B2 | 1/2013 | Iwahori et al. |
| 2002/0084707 A1 | 7/2002 | Tang |
| 2002/0088068 A1 | 7/2002 | Levy et al. |
| 2002/0127512 A1 | 9/2002 | Chen et al. |
| 2002/0196113 A1 | 12/2002 | Rudd et al. |
| 2003/0017874 A1 | 1/2003 | Jianfei et al. |
| 2003/0093103 A1 | 5/2003 | Malackowski |
| 2003/0097723 A1 | 5/2003 | Li |
| 2003/0115694 A1 | 6/2003 | Pace |
| 2004/0060137 A1 | 4/2004 | Eliav |
| 2004/0068811 A1 | 4/2004 | Fulop et al. |
| 2004/0123409 A1 | 7/2004 | Dickie |
| 2004/0128778 A1 | 7/2004 | Wong |
| 2004/0191724 A1 | 9/2004 | Rahman et al. |
| 2004/0255409 A1 | 12/2004 | Hilscher et al. |
| 2005/0011022 A1 | 1/2005 | Kwong |
| 2005/0011023 A1 | 1/2005 | Chan |
| 2005/0037316 A1 | 2/2005 | Sholder |
| 2005/0102776 A1 | 5/2005 | Mathur |
| 2005/0128051 A1 | 6/2005 | Dickinson et al. |
| 2005/0235438 A1 | 10/2005 | Motohashi et al. |
| 2005/0271531 A1 | 12/2005 | Brown, Jr. et al. |
| 2005/0272001 A1 | 12/2005 | Blain et al. |
| 2005/0278877 A1 | 12/2005 | Akridge et al. |
| 2006/0027246 A1 | 2/2006 | Wilkinson |
| 2006/0032006 A1 | 2/2006 | Brown et al. |
| 2006/0048315 A1 | 3/2006 | Chan et al. |
| 2006/0048797 A1 | 3/2006 | Jung et al. |
| 2006/0061236 A1* | 3/2006 | Naka et al. ............ 310/328 |
| 2006/0145871 A1 | 7/2006 | Donati et al. |
| 2007/0000079 A1 | 1/2007 | Mori et al. |
| 2007/0130705 A1 | 6/2007 | Chan et al. |
| 2007/0234493 A1 | 10/2007 | Hilscher et al. |
| 2008/0020351 A1 | 1/2008 | Hilscher et al. |
| 2008/0022470 A1 | 1/2008 | Hilscher et al. |
| 2008/0022501 A1 | 1/2008 | Hilscher et al. |
| 2008/0022503 A1 | 1/2008 | Hilscher et al. |
| 2008/0028549 A1 | 2/2008 | Hilscher et al. |
| 2008/0032265 A1 | 2/2008 | Hilscher et al. |
| 2008/0034515 A1 | 2/2008 | Hilscher et al. |
| 2008/0083075 A1 | 4/2008 | Dickie |
| 2008/0102419 A1 | 5/2008 | Sauter et al. |
| 2008/0196735 A1 | 8/2008 | Wyatt et al. |
| 2008/0209650 A1* | 9/2008 | Brewer et al. ............ 15/22.1 |
| 2008/0254407 A1 | 10/2008 | Benning et al. |
| 2008/0293009 A1 | 11/2008 | Winston |
| 2009/0177125 A1 | 7/2009 | Pilcher et al. |
| 2009/0183324 A1 | 7/2009 | Fischer et al. |
| 2009/0211043 A1 | 8/2009 | Kressner |
| 2009/0241276 A1 | 10/2009 | Hall et al. |
| 2009/0243520 A1 | 10/2009 | Kashiwabara et al. |
| 2009/0320221 A1 | 12/2009 | Masuko |
| 2010/0132139 A1 | 6/2010 | Jungnickel |
| 2010/0301783 A1 | 12/2010 | Luckel et al. |
| 2010/0306934 A1 | 12/2010 | Headstrom |
| 2011/0005015 A1 | 1/2011 | Iwahori et al. |
| 2011/0041268 A1 | 2/2011 | Iwahori et al. |
| 2011/0080122 A1 | 4/2011 | Klemm et al. |
| 2011/0107531 A1 | 5/2011 | Ye |
| 2011/0138551 A1 | 6/2011 | Stopler et al. |
| 2011/0181208 A1 | 7/2011 | Murata |
| 2011/0181209 A1 | 7/2011 | Murata |
| 2011/0181211 A1 | 7/2011 | Murata |
| 2011/0203061 A1 | 8/2011 | Takahashi et al. |
| 2011/0248085 A1 | 10/2011 | Hilscher et al. |
| 2011/0252584 A1 | 10/2011 | Jousma et al. |
| 2011/0258793 A1 | 10/2011 | Jousma et al. |
| 2011/0273153 A1 | 11/2011 | Lepper et al. |
| 2011/0289699 A1* | 12/2011 | Schaefer et al. ............ 15/4 |

(56) References Cited

U.S. PATENT DOCUMENTS

| | | |
|---|---|---|
| 2012/0036659 A1 | 2/2012 | Ziegler et al. |
| 2012/0042742 A1 | 2/2012 | Utsch et al. |
| 2012/0066848 A1 | 3/2012 | Klemm et al. |
| 2012/0151698 A1 | 6/2012 | Schaefer et al. |
| 2012/0198635 A1 | 8/2012 | Hilscher et al. |
| 2013/0025079 A1 | 1/2013 | Jungnickel et al. |
| 2013/0029289 A1 | 1/2013 | Utsch et al. |

FOREIGN PATENT DOCUMENTS

| | | |
|---|---|---|
| CN | 2048697 | 12/1989 |
| CN | 2124686 | 12/1992 |
| CN | 2149877 | 12/1993 |
| CN | 1098888 A | 2/1995 |
| CN | 2332378 | 8/1999 |
| CN | 1520788 A | 1/2004 |
| CN | 1778278 A | 11/2004 |
| CN | 1778279 A | 11/2004 |
| CN | 183043 A | 3/2005 |
| CN | 1843305 A | 4/2005 |
| CN | 1846651 A | 4/2005 |
| CN | 200980058 | 11/2007 |
| CN | 201055092 Y | 5/2008 |
| CN | 201403746 Y | 10/2008 |
| CN | 201295301 Y | 12/2008 |
| CN | 201187899 Y | 1/2009 |
| CN | 101427944 A | 5/2009 |
| CN | 201341578 Y | 11/2009 |
| CN | 20151881 U | 7/2010 |
| DE | 2413524 | 10/1975 |
| DE | 2826008 C2 | 6/1983 |
| DE | 3708801 A1 | 9/1988 |
| DE | 4036373 C2 | 11/1990 |
| DE | 3936714 | 5/1991 |
| DE | 3937852 | 5/1991 |
| DE | 4012413 | 10/1991 |
| DE | 4036479 | 5/1992 |
| DE | 42 01 027 A1 | 7/1992 |
| DE | 3880015 | 9/1993 |
| DE | 4422086 C1 | 6/1994 |
| DE | 4305013 | 8/1994 |
| DE | 19506129 | 2/1995 |
| DE | 19518935 | 5/1995 |
| DE | 94 11 158 U1 | 8/1995 |
| DE | 19627752 A1 | 7/1996 |
| DE | 29608164 | 8/1996 |
| DE | 19628574 | 3/1997 |
| DE | 19545324 | 6/1997 |
| DE | 196 03 851 A1 | 8/1997 |
| DE | 29608167 | 9/1997 |
| DE | 29709865 U1 | 10/1997 |
| DE | 198 03 311 A1 | 8/1999 |
| DE | 29915858 U1 | 9/1999 |
| DE | 198 40 684 A1 | 3/2000 |
| DE | 19832607 | 5/2000 |
| DE | 199 13 945 A1 | 9/2000 |
| DE | 19921677 | 11/2000 |
| DE | 19923104 A1 | 11/2000 |
| DE | 10001502 | 3/2001 |
| DE | 10026513 | 5/2001 |
| DE | 201 12 320 U1 | 10/2001 |
| DE | 19953651 | 10/2001 |
| DE | 10135257 | 2/2002 |
| DE | 10045353 | 3/2002 |
| DE | 10045067 | 4/2002 |
| DE | 10101163 | 7/2002 |
| DE | 4243219 A1 | 12/2002 |
| DE | 10153863 | 5/2003 |
| DE | 10154946 | 5/2003 |
| DE | 102 47 698 | 4/2004 |
| DE | 10 2004 029 684 A1 | 12/2005 |
| DE | 10 2005 045 800 A1 | 4/2007 |
| DE | 197 27 018 B4 | 4/2007 |
| EP | 0024992 | 3/1981 |
| EP | 046169 B | 8/1984 |
| EP | 0085795 | 3/1987 |
| EP | 0285915 | 10/1988 |
| EP | 0294548 A1 | 12/1988 |
| EP | 0300345 | 1/1989 |
| EP | 0435329 | 7/1991 |
| EP | 0440051 | 8/1991 |
| EP | 0391967 B1 | 8/1992 |
| EP | 0624079 | 10/1993 |
| EP | 0634151 | 1/1995 |
| EP | 0787469 A1 | 8/1997 |
| EP | 0848921 A1 | 6/1998 |
| EP | 1 231 706 A2 | 8/2002 |
| EP | 1267664 | 6/2004 |
| EP | 1379149 | 8/2004 |
| EP | 1244373 | 7/2006 |
| EP | 1 696 539 A1 | 8/2006 |
| EP | 1 737 110 A1 | 12/2006 |
| EP | 1 733 700 B1 | 8/2010 |
| EP | 2 262 083 A1 | 12/2010 |
| FR | 2832298 | 5/2003 |
| GB | 1167444 | 10/1969 |
| GB | 1246564 | 9/1974 |
| GB | 2082713 | 3/1982 |
| GB | 2117230 | 10/1983 |
| GB | 2146893 | 5/1985 |
| GB | 2376758 | 12/2002 |
| GB | 2 412 014 A | 9/2005 |
| JP | 1989083268 | 3/1989 |
| JP | 04-087127 | 3/1992 |
| JP | 04-269906 | 9/1992 |
| JP | 05-269024 | 10/1993 |
| JP | 06-014813 | 1/1994 |
| JP | 07-123600 | 5/1995 |
| JP | 07-177932 | 7/1995 |
| JP | 07-194862 | 8/1995 |
| JP | 08-000358 | 1/1996 |
| JP | 08-066325 | 3/1996 |
| JP | 08-117030 | 5/1996 |
| JP | 1996187125 | 7/1996 |
| JP | 08-275961 | 10/1996 |
| JP | 09-252843 | 9/1997 |
| JP | 1998005041 | 1/1998 |
| JP | 10-127346 | 5/1998 |
| JP | 10-243688 | 9/1998 |
| JP | 28-62873 | 3/1999 |
| JP | 199113638 | 4/1999 |
| JP | 11-318951 | 11/1999 |
| JP | 2000-253639 A | 9/2000 |
| JP | 2001-37788 | 2/2001 |
| JP | 2001-197676 | 7/2001 |
| JP | 2001-346816 | 12/2001 |
| JP | 2001/346816 | 12/2001 |
| JP | 2002/045379 | 2/2002 |
| JP | 2002/306867 | 10/2002 |
| JP | 2002/320399 | 10/2002 |
| JP | 2003/250233 | 9/2003 |
| JP | 2003/348888 | 12/2003 |
| JP | 2004/007890 | 1/2004 |
| JP | 2006-280830 | 10/2006 |
| JP | 2007-000693 | 1/2007 |
| JP | 1998137040 | 5/2008 |
| JP | 2009-100523 | 5/2009 |
| JP | 2010-035315 | 2/2010 |
| JP | 2010-125263 | 6/2010 |
| KR | 2003-0091408 | 12/2003 |
| KR | 10-2005-0043071 | 5/2005 |
| KR | 10-2007-0034649 | 3/2007 |
| KR | 10-0752601 | 8/2007 |
| KR | 10-2007-0107198 | 11/2007 |
| KR | 20-2008-0004243 | 10/2008 |
| KR | 10-2009-106306 | 10/2009 |
| NL | C 1030139 | 10/2005 |
| RU | 2 077 349 C1 | 7/1993 |
| RU | 2 129 826 C1 | 5/1999 |
| SE | 531 401 C2 | 3/2009 |
| SU | 749380 | 7/1980 |
| SU | 1542539 | 2/1990 |
| WO | WO 91/06258 | 5/1991 |

(56) References Cited

FOREIGN PATENT DOCUMENTS

| WO | WO 95/33419 | | 12/1995 |
|---|---|---|---|
| WO | WO 97/24079 | | 10/1997 |
| WO | WO 98/24527 | | 6/1998 |
| WO | WO-98/36703 | A1 | 8/1998 |
| WO | WO 98/55274 | | 10/1998 |
| WO | WO 99/20202 | | 4/1999 |
| WO | WO 99/53562 | | 10/1999 |
| WO | WO 00/39768 | | 7/2000 |
| WO | WO 00/42584 | | 7/2000 |
| WO | WO 00/47128 | | 8/2000 |
| WO | WO 00/74591 | | 12/2000 |
| WO | WO 01/08591 | | 2/2001 |
| WO | WO 01/32052 | | 5/2001 |
| WO | WO 01/47392 | | 7/2001 |
| WO | WO 01/91603 | | 12/2001 |
| WO | WO 02/93881 | | 1/2002 |
| WO | WO 02/071972 | A1 | 9/2002 |
| WO | WO 02/083257 | | 10/2002 |
| WO | WO 02/098315 | | 12/2002 |
| WO | WO 03/054771 | | 7/2003 |
| WO | WO 2005/096882 | A1 | 10/2005 |
| WO | WO 2008/015616 | A2 | 2/2008 |
| WO | WO 2008/019864 | A2 | 2/2008 |
| WO | WO 2008/098107 | A2 | 8/2008 |
| WO | WO 2010/106522 | A1 | 9/2010 |
| WO | WO 2010/106850 | A1 | 9/2010 |
| WO | WO 2010/143156 | A1 | 12/2010 |
| WO | WO 2011/044858 | A1 | 4/2011 |
| WO | WO 2011/077289 | A1 | 6/2011 |
| WO | WO 2011/077290 | A1 | 6/2011 |

OTHER PUBLICATIONS

U.S. Appl. No. 13/557,240, filed Jul. 25, 2012, Utsch et al.
U.S. Appl. No. 13/190,284, filed Jul. 25, 2011, Utsch et al.
U.S. Appl. No. 13/213,865, filed Aug. 19, 2011, Klemm et al.
U.S. Appl. No. 13/190,293, filed Jul. 25, 2011, Ziegler et al.
U.S. Appl. No. 13/450,657, filed Apr. 19, 2012, Hilscher et al.
U.S. Appl. No. 13/166,894, filed Jun. 23, 2011, Hilscher et al.
U.S. Appl. No. 12/627,367, filed Nov. 30, 2009, Hilscher et al.
U.S. Appl. No. 11/888,152, filed Jul. 31, 2007, Hilscher et al.
Office Action from U.S. Appl. No. 10/872,075, dated Mar. 24, 2006.
Office Action from U.S. Appl. No. 10/872,075, dated May 15, 2007.
Office Action from U.S. Appl. No. 10/872,075, dated Jun. 4, 2009.
Office Action from U.S. Appl. No. 10/872,075, dated Aug. 1, 2006.
Office Action from U.S. Appl. No. 10/872,075, dated Oct. 31, 2007.
Office Action from U.S. Appl. No. 10/872,075, dated Dec. 10, 2008.
Office Action from U.S. Appl. No. 10/872,075, dated Dec. 27, 2006.
Office Action from U.S. Appl. No. 11/888,386, dated Dec. 3, 2009.
Office Action from U.S. Appl. No. 09/811,080, dated Feb. 3, 2004.
Office Action from U.S. Appl. No. 09/811,080, dated Oct. 1, 2004.
Office Action from U.S. Appl. No. 10/241,274, dated Jan. 14, 2005.
Office Action from U.S. Appl. No. 10/241,274, dated Sep. 1, 2006.
Office Action from U.S. Appl. No. 10/662,237, dated Feb. 18, 2005.
Office Action from U.S. Appl. No. 10/871,469, dated Jan. 9, 2007.
Office Action from U.S. Appl. No. 10/871,469, dated Jul. 25, 2006.
Office Action from U.S. Appl. No. 10/871,469, dated Aug. 24, 2005.
Office Action from U.S. Appl. No. 10/871,469, dated Dec. 27, 2007.
Office Action from U.S. Appl. No. 10/872,016, dated Feb. 7, 2006.
Office Action from U.S. Appl. No. 10/872,016, dated Mar. 7, 2008.
Office Action from U.S. Appl. No. 10/872,016, dated Jun. 24, 2005.
Office Action from U.S. Appl. No. 10/872,016, dated Jul. 10, 2006.
Office Action from U.S. Appl. No. 10/872,016, dated Sep. 20, 2006.
Office Action from U.S. Appl. No. 10/872,016, dated Nov. 9, 2009.
Office Action from U.S. Appl. No. 11/257,603, dated Jan. 18, 2007.
Office Action from U.S. Appl. No. 11/257,603, dated Mar. 21, 2008.
Office Action from U.S. Appl. No. 11/257,603, dated May 15, 2007.
Office Action from U.S. Appl. No. 11/257,603, dated Aug. 30, 2007.
Office Action from U.S. Appl. No. 11/257,603, dated Sep. 20, 2006.
Office Action from U.S. Appl. No. 11/257,603, dated Nov. 25, 2008.
Office Action from U.S. Appl. No. 11/763,338, dated Mar. 24, 2009.
Office Action from U.S. Appl. No. 11/763,338, dated Jul. 10, 2008.
Office Action from U.S. Appl. No. 11/763,338, dated Dec. 4, 2008.
Office Action from U.S. Appl. No. 11/888,212, dated Mar. 17, 2009.
Office Action from U.S. Appl. No. 11/888,251, dated Mar. 17, 2009.
Office Action from U.S. Appl. No. 11/888,251, dated Mar. 21, 2008.
Office Action from U.S. Appl. No. 11/888,386, dated Mar. 3, 2009.
Office Action from U.S. Appl. No. 11/890,083, dated Mar. 16, 2009.
Finkenzeller, Laus, "RFID—Handbuch, Grundlagen und praktische Anwendungen induktiver Funkanlagen, Transponder und kontaktloser Chipkarten" [Trans: "RFID Handbook. Fundamentals and Practical Applications to Inductive Radio Communications, Transponders and Contactless Chip Cards"], Carl Hanser Verlag Munchen, $2^{nd}$ Edtiion, Chapter 3, pp. 29-58 w/title page and Impressum. Contents pp. vii-xviii, and Appendices 15.2 "Standards" and 15.3 "Literature" on pp. 393-406.
Herzer, Gieselher, "Der grosse Lauschangriff auf Ladendiebe" [transl. "The great surveillance of shoplifters"] in Physikalische Blaetter [transl: Physics Letters] vol. 57, (2001), No. 5, pp. 43-48.
Package rear and bottom panels of Bausch & Lomb Interplak Model PB-4B, marked © 1990 (color copy, 1 sheet).
Color photographs of Bausch & Lomb "Interplak" Model PB-6 style Handpiece with waterproof electronic travel protection switch (believed circa 1992 on sale in the United States) (6 views).
Package rear and bottom panels of Bausch & Lomb Interplak Model PB-6, marked © 1992 (color copy, 1 sheet).
Product use instructions to Bausch & Lomb Interplak travel-style "Voyager" model TK-2 marked © 1991 (6 photocopies sheets containing cover and pp. 1-10).
"RFID Made Easy" Handbook by EM Microelectronic-Marin SA, 2074 Marin, Switzerland, copr 2000 and dated Mar. 2001,, Rev. C/350, pp. 1-33.
Use instructions to Braun D5 electric toothbrush Type 4726 on sale in US, circa 1991, including description of "Travel lock" switch.
Color photographs of Bausch & Lomb "Interplak" Model PB-4B style Handpiece with travel protection switch and Toothbrush attachment (handpiece stamped "1D IA", believed circa 1992 on sale in the United States) (2 sheets with 7 views).
PCT Search Report for PCT/EP 01/02844, dated Aug. 8, 2001.
PCT Search Report for PCT/EP 01/02862, dated Jul. 31, 2001.
PCT Search Report for PCT/EP 02/01724, dated Jul. 17, 2002 for U.S. Appl. No. 10/241,274.
PCT International Search Report dated Nov. 2, 2011.
Pct Search Report for PCT/IB2012/053781 dated Jun. 21, 2012.
PCT International search Report dated Oct. 28, 2011.
Office Action from U.S. Appl. No. 10/872,016, dated Feb. 23, 2007.
Office Action from U.S. Appl. No. 10/872,016, dated Apr. 10, 2009.
Office Action from U.S. Appl. No. 11/888,212, dated Mar. 21, 2008.
European Search Report for EP 11 00 6065 dated Feb. 27, 2012.
PCT International Search Report for PCT/IB2011/053665 dated Nov. 23, 2012.
PCT International Search Report for PCT/IB2012/053804 dated Nov. 29, 2012.

* cited by examiner

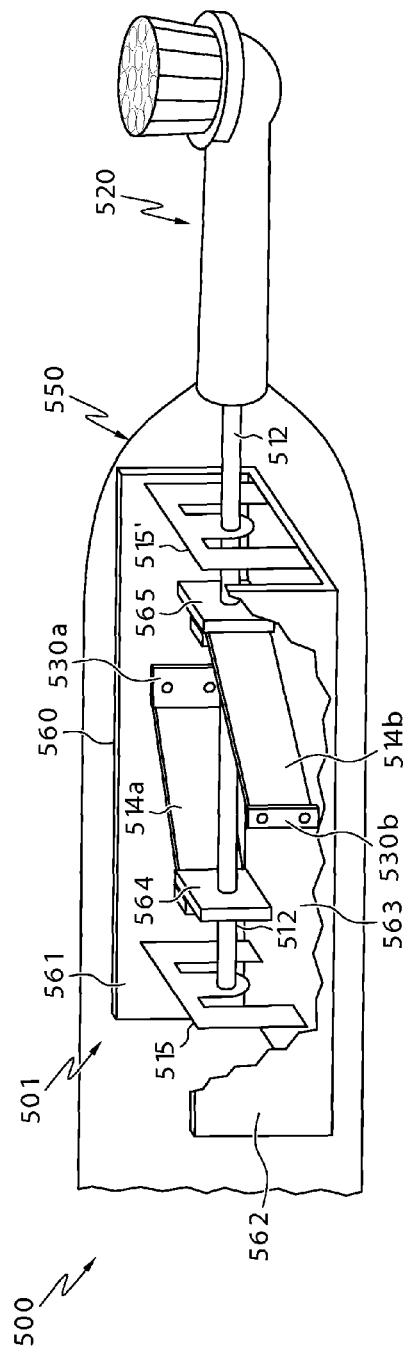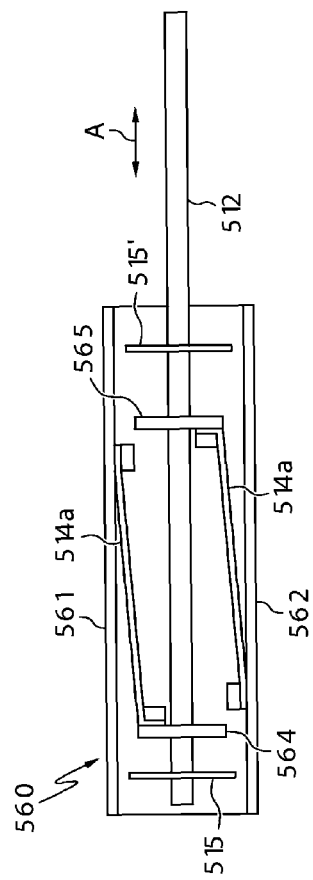
FIG. 5A
FIG. 5B

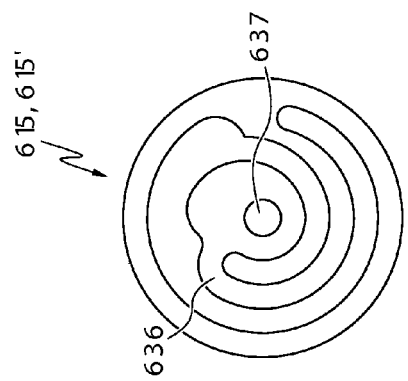
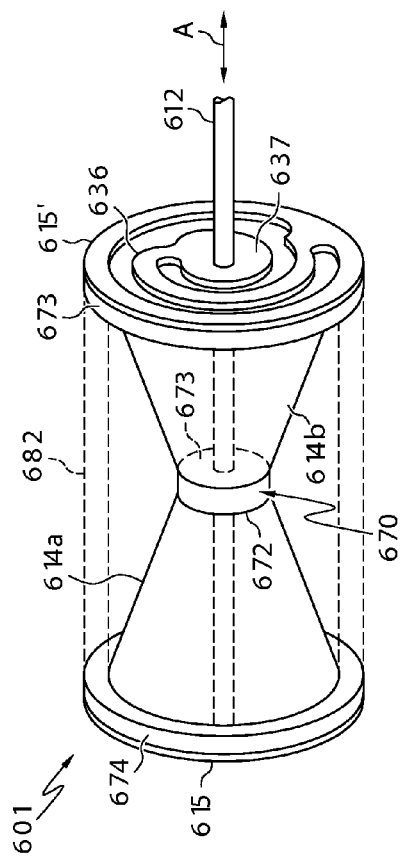
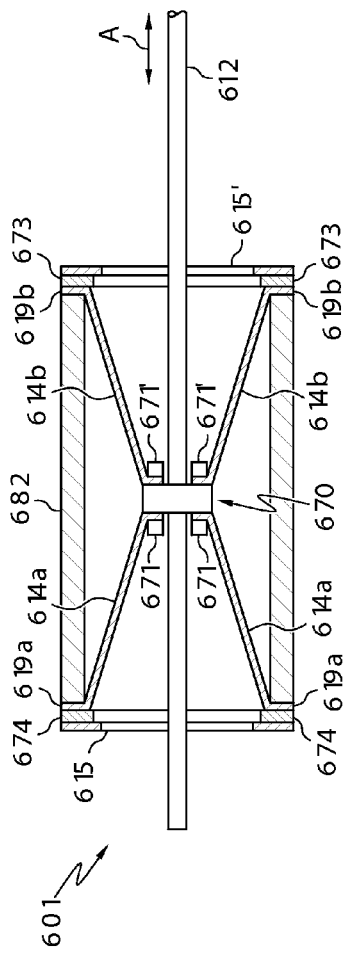

LINEAR ELECTRO-POLYMER MOTORS AND DEVICES HAVING THE SAME

CROSS REFERENCE TO RELATED APPLICATION

This application claims the benefit of U.S. Provisional Application No. 61/511,154, filed Jul. 25, 2011, which is incorporated herein by reference in its entirety.

TECHNICAL FIELD

The present application relates generally to electro-polymer devices and, more particularly, to linear electro-polymer motors and devices incorporating the same.

BACKGROUND

Electro-polymer motors typically have been used in robotics, lens-positioning, and in pumps. Generally, these motors comprise a layer of polymer film situated between two conductive and elastic layers (i.e., electrodes). The polymer can be thought of as a dielectric.

The polymer deforms in response to a voltage that is applied across the pair of electrodes, thereby converting electrical power to mechanical movement.

SUMMARY

In one embodiment, a linear electro-polymer motor includes a fixed member, a linear shaft having an axis, a polymer actuator, and a bias member. The polymer actuator includes a first end and a second end such that the first end of the polymer actuator is fixedly connected to the linear shaft and the second end of the polymer actuator is fixedly connected to the fixed member. The bias member includes a first end and a second end. The first end of the bias member is fixedly connected to the linear shaft, and the second end of the bias member is fixedly connected to the fixed member. The polymer actuator changes length after receipt of voltage to linearly move the linear shaft along the axis.

In another embodiment, a device includes a device housing defining a device enclosure therein, and a linear electro-polymer motor at least partially positioned within the device enclosure defined by the device housing. The linear electro-polymer motor includes a linear shaft having an axis, a polymer actuator, and a bias member. The polymer actuator includes a first end and a second end such that the first end of the polymer actuator is fixedly connected to the linear shaft and the second end of the polymer actuator is fixedly connected to the device housing. The bias member includes a first end and a second end. The first end of the bias member is fixedly connected to the linear shaft, and the second end of the bias member is fixedly connected to the device housing. The polymer actuator changes length after receipt of voltage to linearly move the linear shaft along the axis.

In yet another embodiment, a device includes a device housing and a linear electro-polymer motor. The device housing defines a device enclosure. The linear electro-polymer motor is at least partially positioned within the device enclosure defined by the device housing, and includes an actuator base, a linear shaft having a length, a polymer actuator, a return spring, and a bias member. The actuator base is coupled to the device housing within the device enclosure by an actuator spring. The polymer actuator has a first end and a second end such that the first end of the polymer actuator is fixedly connected to the linear shaft and the second end of the polymer actuator is fixedly connected to the actuator base. The polymer actuator changes length after receipt of voltage. The return spring has a first end fixedly connected to the actuator base and a second end fixedly connected to the linear shaft. The bias member has a first end and a second end such that the first end of the bias member is fixedly connected to the linear shaft, and the second end of the bias member is fixedly connected to the device housing.

In still yet another embodiment, a device includes a base flexibly coupled to an oscillation bridge. The base is located in a first plane and the oscillation bridge is located in a second plane parallel to the first plane. The device further includes a polymer actuator that includes a first end and a second end. The first end of the polymer actuator is coupled to the base and the second end of the polymer actuator is coupled to the oscillation bridge. A voltage applied to the polymer actuator translates the oscillation bridge with respect to the base such that the oscillation bridge linearly travels within the second plane.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The embodiments set forth in the drawings are illustrative in nature and not intended to be limiting of the subject matter defined by the claims. The drawings illustrate various embodiments described herein, and together with the description serve to explain the principles and operations of the claimed subject matter.

FIG. 5A illustrates a partially transparent, side perspective view of an exemplary toothbrush device having an exemplary linear electro-polymer motor according to one or more embodiments described and illustrated herein;

FIG. 5B illustrates a top view of the exemplary linear electro-polymer motor depicted in FIG. 5A;

FIG. 6A illustrates a partially transparent, side perspective view of an exemplary linear electro-polymer motor according to one or more embodiments described and illustrated herein;

FIG. 6B illustrates a top view of an exemplary spring according to one or more embodiments described and illustrated herein;

FIG. 6C illustrates a cross-sectional view of the exemplary linear electro-polymer motor depicted in FIG. 6A;

DETAILED DESCRIPTION OF THE INVENTION

Embodiments disclosed herein are generally related to linear electro-polymer motors that may be incorporated into electronics appliances, such as oral care devices and electric shavers, for example. Polymer actuators may be utilized to drive a driven member, such as a linear shaft, to drive components of the appliance, such as a toothbrush head or razor blades, for example. Various embodiments of the linear electro-polymer motors and devices incorporating the same are described in detail below.

In the following detailed description of the embodiments, reference is made to the accompanying drawings that form a part hereof, and in which are shown by way of illustration, and not by way of limitation, specific embodiments in which the subject matter of the present disclosure may be practiced. It is to be understood that other embodiments may be utilized and that logical, mechanical and electrical changes may be made without departing from the spirit and scope of the present disclosure.

Figure 1:
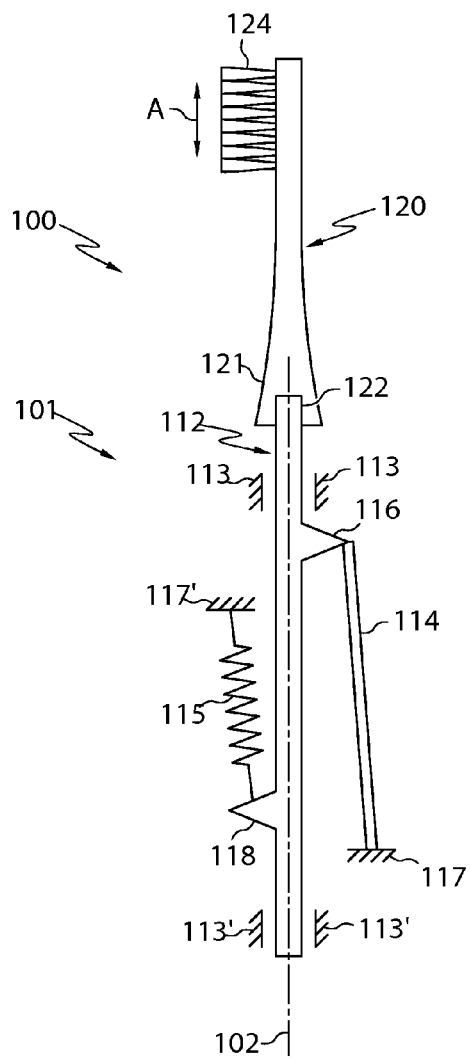
FIG. 1 schematically depicts an exemplary linear electro-polymer motor incorporated into an exemplary toothbrush device according to one or more embodiments described and illustrated herein.

Referring now to FIG. 1, a general schematic of a device 100 having a linear electro-polymer motor 101 is illustrated. Although the embodiments may be described herein in the context of an oral care device, such as an electric toothbrush or a tongue cleaner, embodiments are not limited thereto. For example, various adapters (e.g., adapter 120) may be utilized to change the functionality of the device 100, depending on the desired application.

The linear electro-polymer motor 101 generally comprises a linear shaft 112, a bias member 115, and a polymer actuator 114. The linear shaft 112 may extend along a longitudinal axis 102 and be coupled to a fixed member 117/117' (e.g., a device housing, a motor chassis, or any fixed surface) via the bias member 115 and the polymer actuator 114. As described in more detail herein, the linear shaft 112 may be permitted to linearly translate back and forth along the longitudinal axis 102. For example, a guide 113/113' may be provided, such as a guide sleeve, to limit the linear shaft 112 to one degree of freedom along the longitudinal axis.

As used herein, "linear motion" or "linear movement" is movement along a straight or substantially straight, line or direction. The term "angular motion" refers to any angular displacement. "Curvilinear motion" is movement that is neither completely linear nor completely angular but is a combination of the two (for example, curvilinear). These motions can be constant or periodic. Constant motion refers to motion that does not change direction or path (i.e., is unidirectional). Periodic motion refers to motion that reverses direction or path. Constant angular motion is referred to as rotary motion, although features herein may be described as "rotatably mounted" which is intended to merely mean that angular motion, whether periodic or constant, is possible. Periodic angular motion is referred to as oscillating motion. Curvilinear motions can also be either constant (i.e., unidirectional) or periodic (i.e., reverses direction). Periodic linear motion is referred to as "reciprocation."

The above-described motions can occur along one or more axes of a linear shaft, a device adapter, a bristle carrier, a toothbrush, a toothbrush head, etc. Accordingly, motion is described herein as being either one, two, or three dimensional motion, depending upon the number of axial coordinates required to describe the position of an object during its movement. One dimensional motion is motion that can be described by a single coordinate (for example, X, Y, or Z coordinates). Typically, only linear motion can be one dimensional. For example, periodic linear motion substantially along only the Y axis is one dimensional motion (which may be referred to herein as a "pulsing motion," a "reciprocating motion," "a back and forth motion," or an "up and down motion"). Two dimensional motion is movement by an object that requires two coordinates (for example, X and Y coordinates) to describe the path of travel of the object or objects. Angular motion that occurs in a single plane is two dimensional motion since a point on the object would need two coordinates to describe the path of travel.

Although the various linear shafts may be illustrated as a cylindrical rod, embodiments are not limited thereto. In one embodiment, the linear shaft may be rectangular in cross section (e.g., a bar). Further, the linear shaft of one embodiment may be configured as a plate rather than a cylindrical rod such that the plate defines an axis or direction for axial (linear) motion. The linear shaft may take on any geometric configuration such that it may linearly translate back and forth in a reciprocating manner. Additionally, various components described hereinbelow may be features of the linear shaft rather than discrete components (e.g., springs).

The linear shaft 112 may include an actuator connection region 116 to which one end of the polymer actuator 114 may be fixedly connected, and a bias member connection region 118 to which one end of the bias member 115 may be fixedly connected. In one embodiment, the actuator connection region 116 may be offset from the bias member connection region 118 along the length of the linear shaft 112. Alternatively, the actuator connection region 116 may be at the same location as the bias member connection region 118. In one embodiment, the actuator connection region 116 and the bias member connection region 118 may be configured as an actuator protrusion (or protrusions) that extends from the linear shaft 112 to which the polymer actuator 114 and the bias member 115 may be connected. The polymer actuator 114 and/or the bias member 115 may be connected to the actuator connection region 116 and the bias member connection region 118, respectively, by a variety of means, such as adhesive, laser tacking, mechanical clamping, fasteners, etc.

The polymer actuator 114 may comprise a polymer material that is positioned between a pair of electrodes (not shown). The pair of electrodes may be attached to the opposite surfaces of the polymer actuator in a variety of ways, including but not limited to adhesives, sonic welds, mechanical connectors, coatings, etc. The pair of electrodes may be in communication with a power supply (not shown). The pair of electrodes may apply a voltage across the polymer material resulting in deformation of the polymer material (i.e., the polymer material may expand and/or contract in response to the applied voltage) in a multitude of directions (i.e., lengthwise, widthwise, diagonally, etc.). The power supply may repeatedly and alternately apply and remove power (i.e., voltage) to and from the electrodes of the polymer actuator to cause the linear shaft to oscillate back and forth. Polymer materials and electrodes suitable for use, as well as various voltage control methods, are further described in U.S. Pat. Nos. 6,545,384 and 6,781,284 and U.S. Pat. Pub. No. 2010/0043157, which are herein incorporated by reference for all purposes.

A first end of the polymer actuator 114 may be fixedly coupled to actuator connection region 116 of the linear shaft 112, and a second end may be fixedly coupled to the fixed member at a first connection region 117. The length of the polymer actuator 114 may depend on the amount of travel that is desired for the particular application in which the linear electro-polymer motor 101 is to be implemented.

The bias member 115, which may be configured as a spring, comprises a first end that may be fixedly coupled to the bias member connection region 118 of the linear shaft 112 and a second end that may be fixedly connected to the fixed member at a connection region 117'. The bias member 115 and the polymer actuator 114 cooperate to drive the linear shaft 112 in one dimension (i.e., the axial direction), as indicated by arrow A. By applying a voltage to the electrodes of the polymer actuator 114, the polymer actuator 114 may expand, thereby allowing the linear shaft 112 to move in the upward direction. When the voltage is switched off, the polymer actuator 114 may shorten and move the linear shaft 112 downward. The bias member 115 may aid in the axial movement of the linear shaft 112 by providing a spring force. By alternating the voltage between ON and OFF states, the linear shaft 112 may linearly translate back and forth along its axis at a desired frequency. The desired frequency of the back and forth movement of the linear shaft 112 may depend on the particular application. In the context of an electric toothbrush, in one embodiment the frequency of translation may be in the range of about 50 Hz to about 500 Hz. In another embodiment, the frequency of translation may be in the range of about 100 Hz to about 200 Hz. In yet another embodiment, the frequency of translation is about 150 Hz. It should be understood that other translation frequencies may be utilized depending on the particular application.

The linear electro-polymer motor 101 may be utilized in a variety of small appliance applications, such as electric toothbrushes, tongue cleaners, woodworking tools, electric shavers, etc. The linear electro-polymer motor 101 may be coupled to adapters 120 that may be configured for use in particular applications. The adapter 120 illustrated in FIG. 1 is a toothbrush head such that the device 100 is configured as an electric toothbrush. In this embodiment, the linear electro-polymer motor 101 may be maintained in a device housing that acts as the fixed member such that the linear shaft 112 translates with respect to the housing. The adapter 120 illustrated in FIG. 1 has a first end 121 that may be coupled to the linear shaft 112 by an engagement feature 122. In one embodiment, the engagement feature 122 provides an interference fit or a removable snap fit such that the adapter 120 may be removed from the linear shaft 112. Contact elements 124 may be provided at a second end of the adapter. Periodic linear movement of the linear shaft 112 along its axis drives the contact elements 124 as indicated by arrow A, which may aid in the efficacy of tooth brushing. Contact elements are discussed in further detail hereafter.

The adapter 120 may comprise any number of known and unknown shapes, sizes, configurations, and materials. Exemplary materials for the adapter 120 may include, but are not limited to, polymers, plastics, elastomers, metals, composites, or combinations thereof (e.g., polypropylene, POM, ASA, ABS, PC, SAN or any other suitable material).

Figure 2:
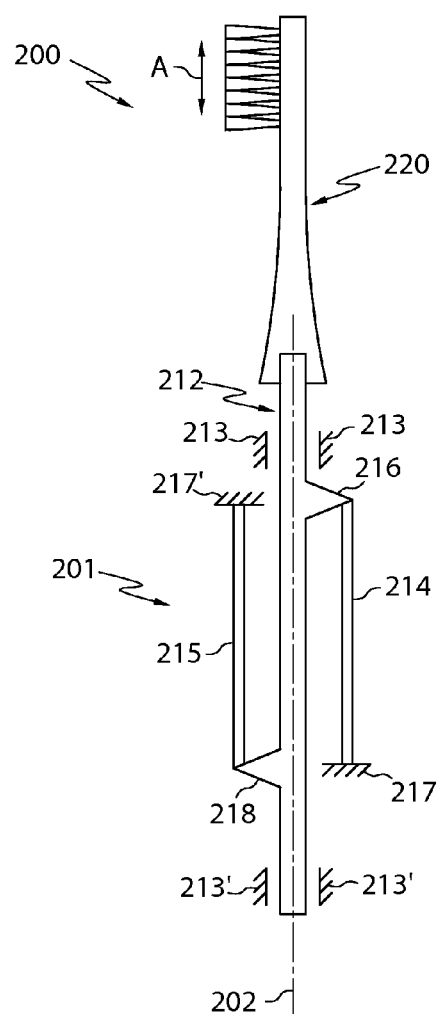
FIG. 2 schematically depicts an exemplary linear electro-polymer motor incorporated into an exemplary toothbrush device according to one or more embodiments described and illustrated herein.

Referring now to FIG. 2, a device 200 having a linear electro-polymer motor 201 that replaces bias member 115 of FIG. 1 with a second polymer actuator 215 is illustrated. In this embodiment, a first polymer actuator 214 may be fixedly connected to the actuator connection region 216 and the fixed member at the first connection region 217. The second polymer actuator 215 may be fixedly connected to the bias member connection region 218 and the second connection region 217'. Alternating voltages may be provided to the first and second polymer actuators 214, 215 such that the two polymer actuators work in opposite directions and act as agonist and antagonist. For example, a first sinusoidal voltage may be provided to the first polymer actuator 214 and a second sinusoidal voltage may be provided to the second polymer actuator 215, wherein the first and second sinusoidal voltages may be out of phase with respect to one another such that the first and second polymer actuators are alternately actuated, thereby causing the linear shaft 212 to move back and forth. Methods of controlling the first and second polymer actuators 214, 215 are provided in U.S. Pat. Pub. No. 2010/0043157, which is herein incorporated by reference in its entirety.

Figure 11B:
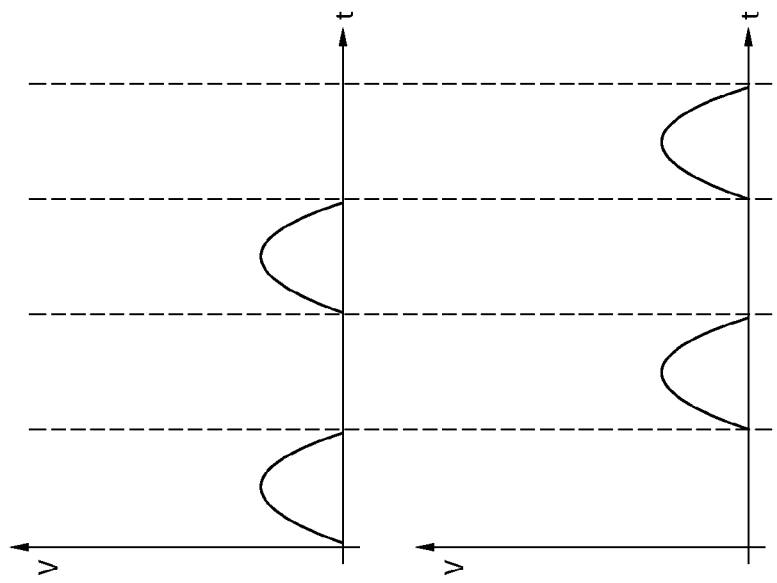
FIG. 11B illustrates an exemplary sinusoid oscillating voltage pattern according to one or more embodiments described and illustrated herein.
Figure 11A:
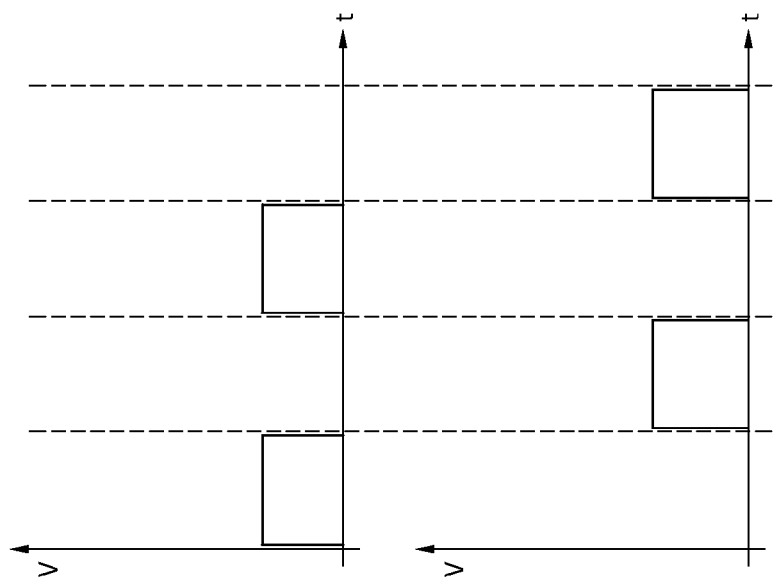
FIG. 11A illustrates an exemplary digital oscillating voltage pattern according to one or more embodiments described and illustrated herein.

In embodiments that utilize two polymer actuators that operate to move the linear shaft in opposing directions (e.g., the first and second polymer actuators 214 and 215 depicted in FIG. 2), the power supply may alternate power between a first polymer actuator and a second polymer actuator using an oscillating pulse resulting in the linear shaft 212 oscillating along its axis 202. FIG. 11A illustrates an oscillating pulse voltage in a step function that may be delivered to the polymer actuators. Specifically, the power supply may apply a voltage across the pair of electrodes associated with the first polymer actuator while applying zero voltage across the pair of electrodes associated with the second polymer actuator, and then applying zero voltage to the pair of electrodes associated with the first polymer actuator, while applying a voltage across the pair of electrodes associated with the second polymer actuator. This alternating power may be repeated for any amount of time required to perform a task. Alternatively, FIG. 11B illustrates that an oscillating pulse voltage may be configured as a sinusoidal function. The oscillating pulse, in one exemplary embodiment, may apply a positive voltage (the pulse wave above the t-line) to the first polymer actuator while the negative voltage (the pulse wave below the t-line) may be inverted and applied to the second polymer actuator.

Figure 10C:
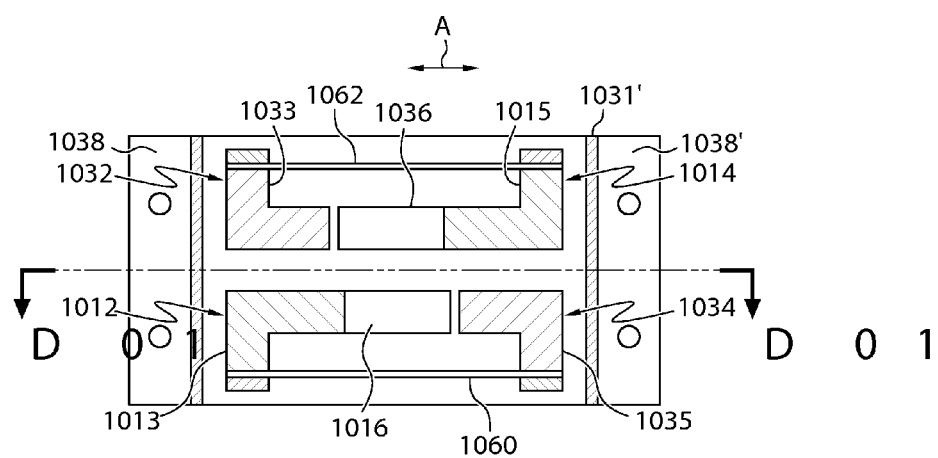
FIG. 10C illustrates a cross-sectional view of the exemplary electric shaver device depicted in FIG. 10B.
Figure 11C:
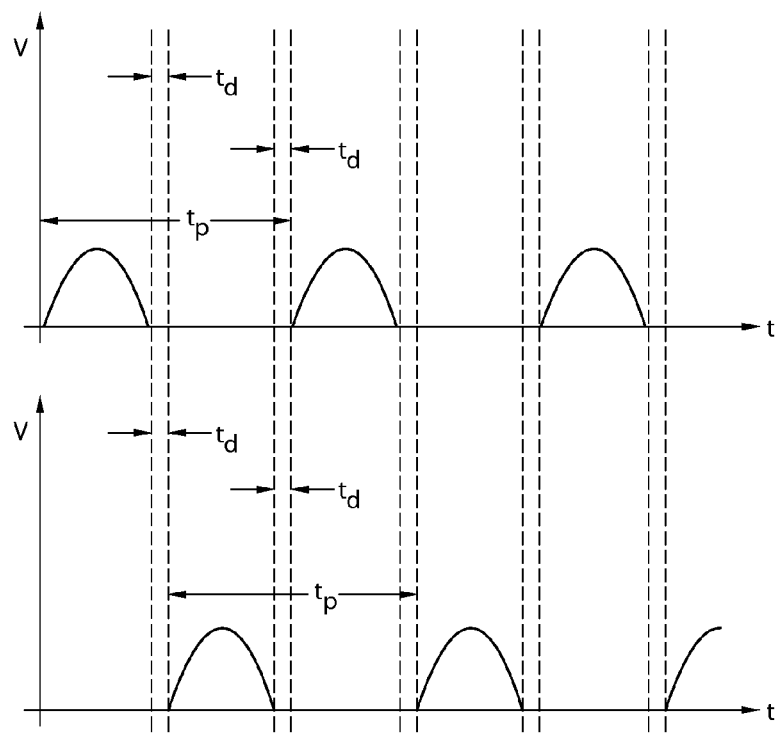
FIG. 11C illustrates an exemplary sinusoid oscillating voltage pattern according to one or more embodiments described and illustrated herein.

FIG. 11C illustrates an oscillating pulse voltage wherein a delay $t_d$ is provided after a voltage pulse applied to one of the polymer actuators and before application of a voltage pulse to the other, second polymer actuator. The oscillating pulse voltage, which may be sinusoidal as depicted in FIG. 10C in one embodiment, may have a period $t_p$ that incorporates the delay $t_d$. The delay $t_d$ may allow the polymer actuator to begin to go back to its pre-strained state prior to activating the other polymer actuator with the application of voltage. The duration of period $t_p$ and delay $t_d$ may depend on the particular application in which the linear electro-polymer motor is implemented.

Figure 12A:
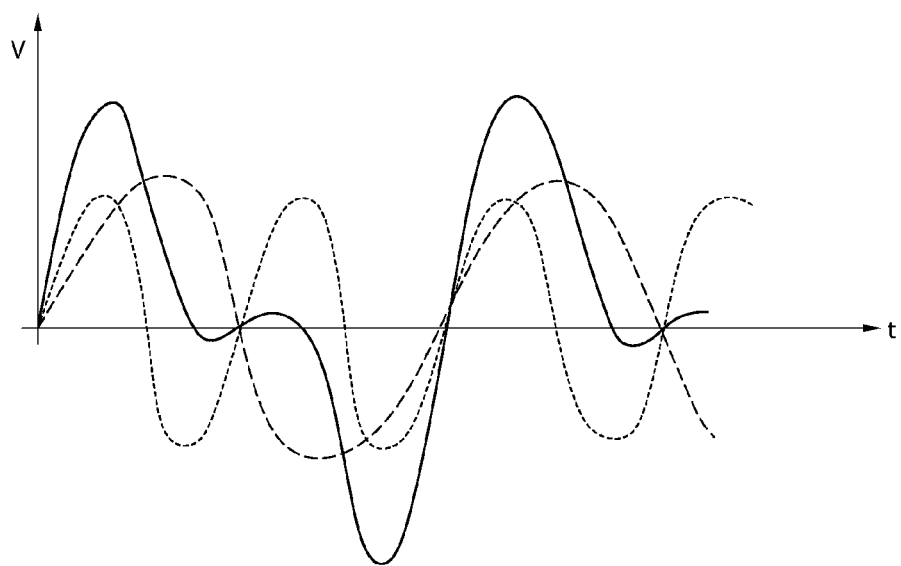
FIG. 12A illustrates an exemplary sinusoid voltage pattern for two different oscillation frequencies according to one or more embodiments described and illustrated herein.
Figure 12B:
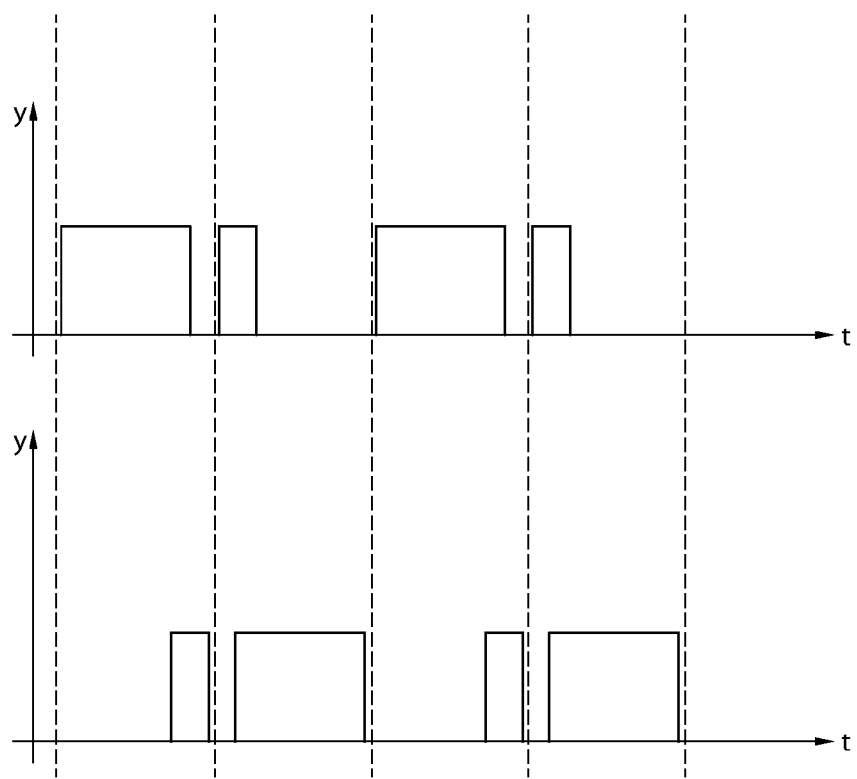
FIG. 12B illustrates an exemplary digital voltage pattern for two different oscillation frequencies according to one or more embodiments described and illustrated herein.

Alternatively, the power supply may supply substantially concurrent power to the first and second polymer actuators using a pulsating pulse resulting in the linear shaft moving along its axis. Again, the pulsating pulse may be sinusoid. A controller (not shown) may control the amount of voltage the power supply applies to the pairs of electrodes of the first and second polymer actuators. Additionally, the controller may control the frequency of the pulse pattern. The controller may control the frequency to be between about 0.1 Hz to about 150 kHz, or more specifically between 0.5 Hz to about 100 kHz, and even more specifically between 1 Hz to about 50 kHz. The controller may also overlay the oscillating and pulsating pulse frequencies to produce the linear motion of the linear shaft as shown in FIGS. 12A and 12B.

Referring once again to FIG. 2, a guide 213/213' may be provided to ensure that the linear shaft 212 moves in a linear direction as indicated by arrow A. This embodiment may generate higher forces at the linear shaft 212 than the embodiment illustrated in FIG. 1. Similar to the embodiment illustrated in FIG. 1, an adapter 220 may be provided, such as a toothbrush head.

Figure 3:
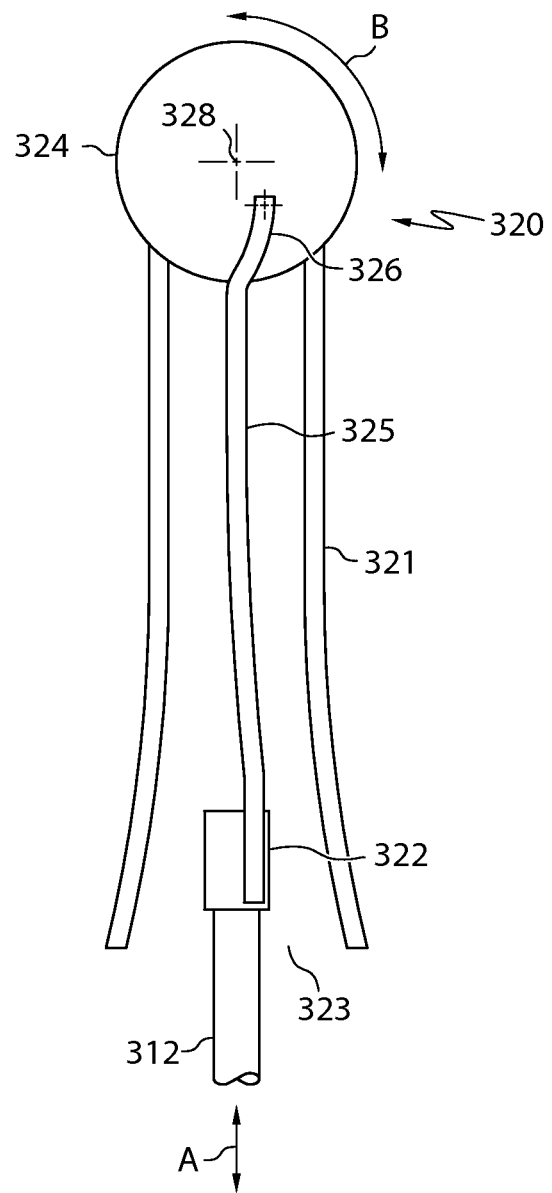
FIG. 3 schematically depicts an exemplary adapter having a rotating member according to one or more embodiments described and illustrated herein.

Referring now to FIG. 3, an adapter 320 according to one embodiment is illustrated. The adapter 320 generally comprises a rotating member 324 (e.g., a disk having toothbrush bristles in an electric toothbrush application), a push rod 325, a rocker arm 326, and an adapter housing 321. The push rod 325 and the rocker arm 326 may be disposed within an adapter recess 323 defined by the adapter housing 321. A coupling feature 322 may be provided at a coupling end of the push rod 325 such that the push rod 325 may be removably coupled to the linear shaft 312. In one embodiment, the push rod 325 may be positioned at an angle with respect to the linear shaft 312 to aid in periodic angular movement of the rotating member 324. The rocker arm 326 may be located at an end of the push rod 325 that is distal from the coupling feature 322. The rocker arm 326 and the push rod 325 may be integral components or two separate components.

The rocker arm 326 may be coupled to the rotating member 324 at a location that is offset from a central axis of rotation 328 of the rotating member 324, wherein the periodic linear movement of the linear shaft 312 (arrow A) translates the push rod 325 such that the rocker arm 326 oscillates the rotating member 324 about a rotational axis 328 as indicated by arrow B. In this manner, the push rod 325 and the rocker arm 326 transform the periodic linear movement of the linear shaft 312 into periodic angular movement of the rotating member 324. In this embodiment, the rotating member 324 rotates as indicated by arrow B. In one embodiment, the oscillating rotation of the rotating member 324 is between about 1 degree and about 179 degrees about a rotational axis. In another embodiment, the oscillating rotation of the rotating member 324 is between about 20 and 40 degrees about the rotational axis. In further embodiments, the oscillating rotation of the rotating member 324 may be greater than about 5 and less than about 20.

In an electric toothbrush embodiment, a user may selectively couple a rotating toothbrush head adapter 320 as illustrated in FIG. 3 to have an electric toothbrush with a brushhead that rotates or linearly translates. As such, in one embodiment the user may also selectively couple an adapter as illustrated in FIGS. 1 and 2 for an electric toothbrush head that only linearly translates along its axis. The user may choose the desired brush form by only exchanging the toothbrush head.

Figure 4:
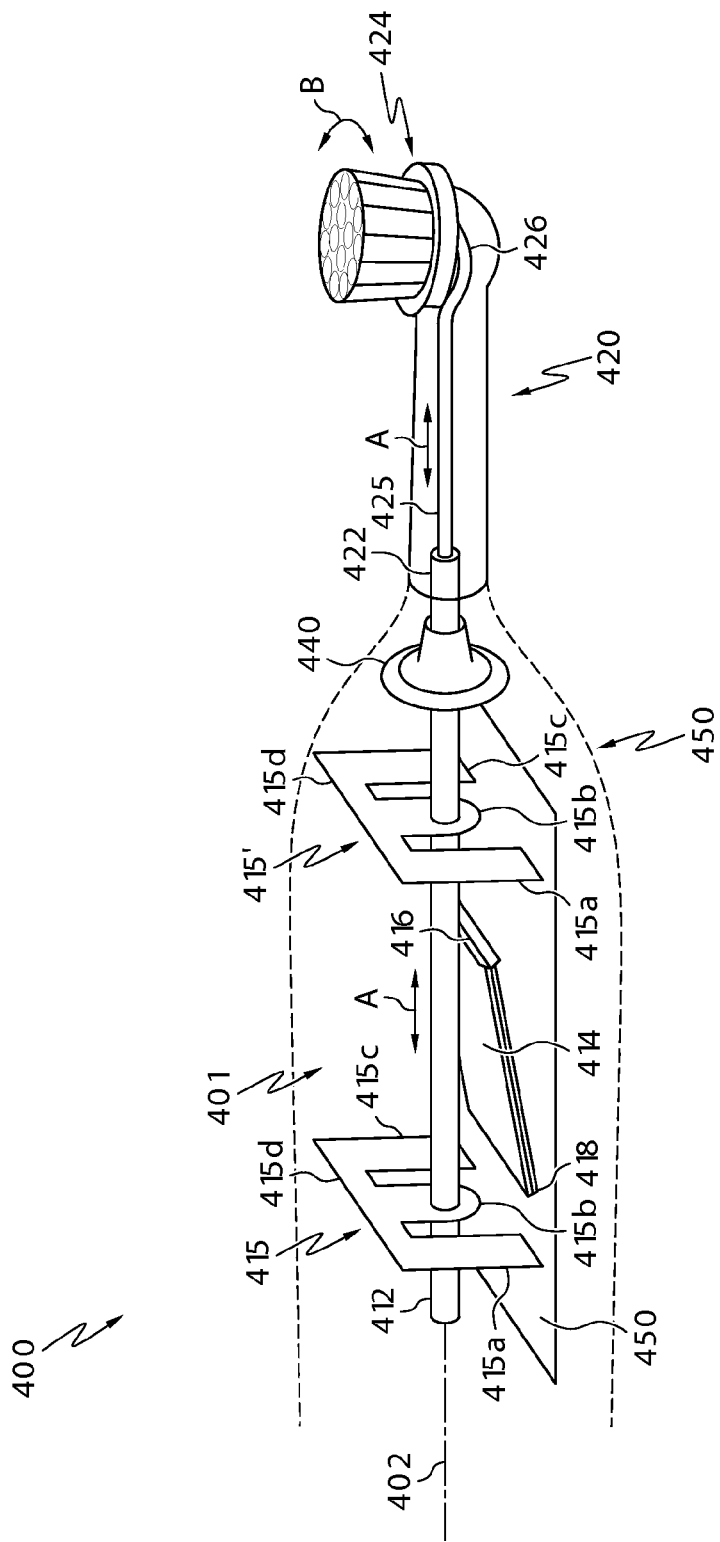
FIG. 4 illustrates a partially transparent, side perspective view of an exemplary toothbrush device having an exemplary linear electro-polymer motor according to one or more embodiments described and illustrated herein.

FIG. 4 illustrates a device 400 (electric toothbrush) having a linear electro-polymer motor 401 as schematically depicted in FIG. 1. The device 400 generally comprises a device housing 450 (which acts as a fixed member), a linear electro-polymer motor 401 disposed within a device enclosure defined by the device housing 450, and an adapter 420 coupled to the device housing. The linear shaft 412 of the linear electro-polymer motor 401 may be disposed within the device enclosure along axis 402, and positioned through a first flat spring 415, a second flat spring 415', and a bellow seal 440. A first end of the polymer actuator 414 may be fixedly connected to the linear shaft 412 at the actuator connection region 416 by any number of connection means, as described above. A second end of the polymer actuator 414 may be fixedly connected to the device housing 450 at the first connection region 418 by any number of connection means (e.g., by fasteners, tacking, adhesives, solder, etc.).

As shown in FIG. 4, the bias member 115 depicted in FIG. 1 is configured as the first and second flat springs 415, 415', which may be fixedly connected to the linear shaft 412. The first and second flat springs 415, 415' may take on a variety of configurations. Further, more or fewer flat springs may be utilized. The first and second flat springs 415, 415' may comprise a compliant material to provide a springing force to the linear shaft 412. Exemplary materials may include, but are not limited to, metal, plastic, composites, elastomers, polymers, and the like.

The first and second flat springs 415, 415' of the illustrated embodiment are M-shaped and have a first end 415d, and two outer arms 415a, 415c and a middle arm 415b that extend from the first end 415d. The first end 415d may or may not be coupled to the device housing 450. In the illustrated embodiment, the two outer arms 415a, 415c are fixedly connected to the device housing 450 while the middle arm 415b is not fixedly connected to the device housing 450. The middle arm 415b may form a cantilever spring portion through which the linear shaft 412 is positioned. The middle arm 415b of the first and second flat springs 415, 415' may comprise a shaft-receiving through-hole through which the linear shaft 412 is positioned. In an alternative embodiment, the flat springs may comprise only an upper portion (e.g., first end 415d) and a cantilever portion extending therefrom (e.g., middle arm 415b). In this embodiment, the flat springs do not have the two outer arms such that only the cantilever portion extends from the first end. It should be understood that other spring configurations are also possible.

The first and second flat springs 415, 415' may be fixedly connected to the linear shaft 412 by any means. For example, the first and second flat springs 415, 415' may be fixedly connected by adhesive, tacking, soldering, use of fasteners, etc. In an alternative embodiment, the first and second flat springs 415, 415' may be integral with the linear shaft 412. The configuration of the first and second flat springs 415, 415' act as a return (i.e., bias) spring as well as a guiding spring to perform the function of the guiding sleeve 113 illustrated in FIG. 1.

A seal such as the bellow seal 440 illustrated in FIG. 4 may be provided to keep water and other foreign substances from entering the device enclosure defined by the device housing 450. The bellow seal 440, which may take on a variety of configurations, may protect the linear electro-polymer motor 401 and power supply maintained within the device housing 450. The bellow seal 440 may be made of polymer, rubber, or any other suitable material. The adapter 420 may be coupled to the device housing 450 via the coupling feature 422 such that the linear shaft 412 is removably coupled to the push rod 425. The periodic linear movement of the linear shaft 412 may translate to oscillating angular movement of the rotating member 424 via the pusher rod 425 and the rocker arm 426. In one embodiment, the oscillating rotation of the rotating member 424 is between about 1 degree and about 179 degrees about a rotational axis. In another embodiment, the oscillating rotation of the rotating member 424 is between about 20 and 40 degrees about the rotational axis.

The device housing 450 may comprise any number of known and unknown shapes, sizes, configurations, and materials. Exemplary materials for the device housing 450 may include, but are not limited to, polymers, plastics, elastomers, metals, composites, or combinations thereof (e.g., polypropylene, POM, ASA, ABS, PC, SAN or any other suitable material).

Referring now to FIGS. 5A and 5B, a device 500 having a dual polymer actuator linear electro-polymer motor as schematically depicted in FIG. 2 is illustrated. The device 500, which is illustrated as an electric toothbrush, generally comprises a device housing 550, a linear electro-polymer motor 501 disposed within a device enclosure defined by the device housing 550, and an adapter 520. The exemplary linear electro-polymer motor 501 comprises a chassis 560 that may be fixedly connected to the device housing 550 within the device enclosure, a linear shaft 512, a first polymer actuator 514a, a second polymer actuator 514b, a first flat spring 515, and a second flat spring 515'.

The U-shaped chassis 560 may comprise a support wall 563 (i.e., a bottom surface), a first side wall 561, and a second side wall 562. A portion of the second side wall 562 is illustrated as removed in FIG. 5A for visibility purposes. The chassis 560 may be made of a rigid material, such as, without limitation, metal, plastic, polymers, elastomers, composites, or combinations thereof. The chassis 560 may provide a mounting structure for the polymer actuators and the flat springs.

The linear shaft 512 may be fixedly connected to the first and second flat springs 515, 515' as described above. The first and second flat springs 515, 515' may be fixedly connected to the support wall 563 of the chassis at the two outer arms, while the middle arm may be free. As shown in FIGS. 5A and 5B, the first and second flat springs 515, 515' may be offset from one another along the linear shaft 512 in one embodiment.

The linear electro-polymer motor 501 may further comprise first and second actuator coupling plates 564, 565 that coupled the first and second polymer actuators 514a, 514b to the linear shaft 512, respectively. A first end of the first polymer actuator 514 may be fixedly connected to the first actuator coupling plate 564 (by a clamping force, for example), which may be fixedly connected to the linear shaft 512 positioned within a through-hole. In an alternative embodiment, the linear shaft 512 and the first actuator coupling plate 564 may be an integral, single component. A second end of the first polymer actuator 514a may be fixedly connected to the first side wall 561 of the chassis 560. In the exemplary embodiment, a third actuator coupling plate 530a is used to connect the first polymer actuator 514a to the first side wall 561. Fasteners may be used to connect the third actuator coupling plate 530a and the first polymer actuator 514a to the first side wall 561. Other coupling methods may also be utilized to connect the first polymer actuator 514a to the linear shaft 512 and/or the first side wall 561 of the chassis 560.

Similarly, a first end of the second polymer actuator 514b may be fixedly connected to the second actuator coupling plate 565 (by a clamping force, for example), which may be fixedly connected to the linear shaft 512 positioned within a through-hole. As with the first actuator coupling plate, the second actuator coupling plate 565 may be integral with the linear shaft 512. A second end of the second polymer actuator 514b may be fixedly connected to the second side wall 562 of the chassis 560. In the exemplary embodiment, a fourth actuator coupling plate 530b is used to connect the second polymer actuator 514b to the second side wall 562. Fasteners may be used to connect the fourth actuator coupling plate 530b and the second polymer actuator 514b to the second side wall 562. Other coupling methods may also be utilized to connect the second polymer actuator 514b to the linear shaft 512 and/or the second side wall 562 of the chassis 560.

The two polymer actuators may be mounted in parallel to each other and arranged such that each moves the linear shaft in opposing directions. The first and second polymer actuators may be controlled as described above with respect to FIG. 2, or by other control methods. The flat springs may be configured to guide the linear shaft in a frictionless and playless manner.

Referring now to FIGS. 6A-6C, another dual polymer actuator embodiment is illustrated. FIG. 6A illustrates a side perspective view of a linear electro-polymer motor 601 having a first polymer actuator 614a, a second polymer actuator 614b, a first spring 615, and a second spring 615'. FIG. 6B is a top view of an exemplary spring according to one embodiment. FIG. 6C is a side view of the linear electro-polymer motor 601 depicted in FIG. 6A. The first and second polymer actuators 614a, 614b may have a conical shape in the pre-strained state, and may have a large diameter end and a small diameter end. The linear shaft 612 may be axially positioned through the first and second polymer actuators 614a, 614b. The small diameter end of the first and second polymer actuators 614a, 614b may be fixedly connected to the linear shaft 612 by a ring 670. The linear shaft 612 may be positioned through a central hole of the ring 670 and secured in place. In an alternative embodiment, the ring 670 is integral with the linear shaft 612.

The small diameter end of the first polymer actuator 614a may be connected to a first surface 672 of the ring 670, and the small diameter end of the second polymer actuator 614b may be connected to a second surface 673 of the ring 670. The polymer actuators may be fixedly connected to the ring 670 by one or more clamping devices 671, 671'. Any connection configuration may be utilized to fixedly connect the small diameter ends of the first and second polymer actuators 614a, 614b to the ring 670.

In one embodiment, the first and second polymer actuators 614a, 614b may be maintained within an actuator cavity defined by a motor housing 682. The motor housing 682 may be cylindrical in shape, for example, and be made of a rigid material. The motor housing 682 may be fixedly connected to the device housing of a device, such as an electric toothbrush. In one embodiment, the large diameter ends of the first and second polymer actuators 614a, 614b define a large end flange portion 619a, 619b that may be secured to the motor housing 682 by first and second clamping rings 673, 674, respectively. Any clamping or securing method may be utilized to secure the large end flange portions 619a, 619b to the motor housing 682.

The first spring 615 and the second spring 615' may be coupled to the first and second clamping rings 673, 674 or other clamping device used to secure the first and second polymer actuators 614a, 614b to the motor housing 682. Therefore, the first and second springs 615, 615' may be fixedly connected to the motor housing 682 and the large diameter end of the first and second polymer actuators 614a, 614.

As shown in FIG. 6B, the first and second springs 615, 615' may comprise a spiral arm 636 that ends in a central termination region 637 that may be configured to be fixedly connected to a linear shaft 612 positioned therethrough. The first and second springs 615, 615' may be made of a compliant material, such as those described above with respect to the flat springs. The spiral arm 636 may act as a cantilever spring that enables co-axial positioning of the linear shaft 612 with respect to the first and second polymer actuators 614a, 614b. The first and second springs 615, 615' guide the linear shaft 612 such that the linear shaft may linearly travel as indicated by arrow A.

The first and second polymer actuators 614a, 614b may alternately deform with the application of voltage as described above to move the ring 670 and the linear shaft 612 back and forth as indicated by arrow A. The first and second polymer actuators 614a, 614b may cooperate to translate the linear shaft 612, which may be coupled to an adapter as described above.

Figure 7A:
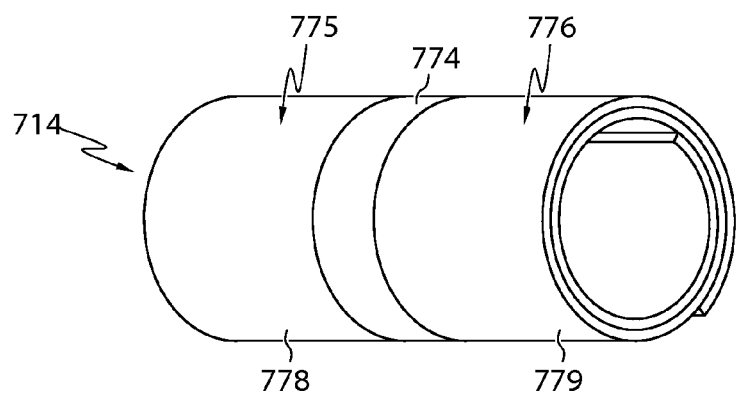
FIG. 7A illustrates a side perspective view of an exemplary rolled polymer actuator according to one or more embodiments described and illustrated herein.
Figure 7B:
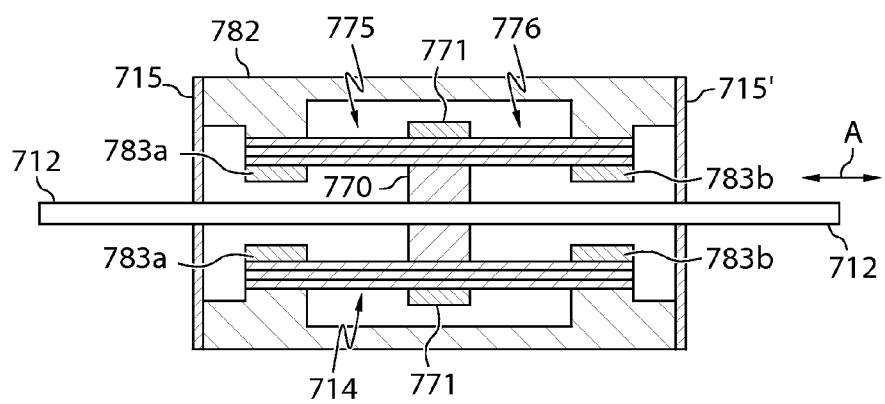
FIG. 7B illustrates a cross-sectional view of an exemplary linear electro-polymer motor having the exemplary rolled polymer actuator depicted in FIG. 7A according to one or more embodiments described and illustrated herein.

FIGS. 7A and 7B depict a dual polymer actuator 714 wherein the first and second polymer actuators 775, 776 may be realized on the same polymer layer. In the illustrated embodiment, the first and second polymer actuators 775, 776 comprise a polymer layer having two addressable electrode areas 778, 779 that define the first and second polymer actuators 775, 776. Each electrode area 778, 779 has a first electrode on a first side and a second electrode on the opposing side. The polymer layer may be rolled or wound such that the rolled dual polymer actuator 714 may comprise at least one roll layer. Exemplary rolled polymer actuators are described in U.S. Pat. No. 6,891,317, which is herein incorporated by reference in its entirety. A first electrode area 778 controls the first polymer actuator 775, and a second electrode area 779 controls the second polymer actuator 776. A non-deforming region 774 may be located between the first electrode area 778 and the second electrode area 779. The non-deforming region 774 may not comprise an electrode area and therefore not be subjected to the application of voltage, thereby remaining static.

Referring now to FIG. 7B, the polymer layer may be rolled about a circular actuator plate 770 that may be fixedly coupled to the linear shaft 712. The actuator plate 770 may be connected to the non-deforming region 774 of the rolled polymer actuator. The polymer layer may be fixedly connected to the actuator plate 770 by any means. In one embodiment, a clamping device 771 may be utilized to clamp the rolled polymer layer to the actuator plate 770. Other coupling methods may be used. The rolled, dual polymer actuator 714 may be fixedly maintained within a motor housing 782, which may be made of a rigid material, such as metal, plastic, polymers, etc. The motor housing 782 may be fixedly connected to a device housing (not shown). First and second ends of the rolled dual polymer actuator 714 may be fixedly connected to ends of the rolled polymer actuator by any means, such as by the use of clamps 783a and 783b. Other connection methods may be used, such as by the use of an adhesive, tacking, fasteners, etc., for example.

A first spring 715 may be fixedly connected to a first end of the motor housing 782 and a second spring 715' may be fixedly connected to a second end of the motor housing 782. In one embodiment, the first and second springs 715, 715' may be configured as the springs illustrated in FIGS. 6A-6C such that the linear shaft 712 is positioned through, and fixedly connected to, a central termination region. In this manner, the linear shaft 712 may be positioned within a cylindrical opening defined by the rolled dual polymer actuator 714. The first and second springs 715, 715' may aid in guiding the linear shaft 712 such that it has only one degree of freedom along its axis.

The ends of the rolled dual polymer actuator 714 may be fixedly connected to the ends of the motor housing 782. The central, non-deforming region 774 of the rolled dual polymer actuator 714 may be fixedly connected to the actuator plate 770 and the linear shaft 712. Therefore, alternating voltages applied to the first and second electrode areas 778, 779 cause the first and second polymer actuators 775, 776 to alternately expand, thereby translating the actuator plate 770 and the linear shaft 712, as indicated by arrow A. The linear shaft 712 may be coupled to an adapter, as described above.

In an alternative embodiment, the linear electro-polymer motor may comprise a single, rolled polymer actuator having a single active region. In this example, one of the polymer actuators (e.g., first polymer actuator 775) is replaced by a spring (or springs) such that the spring provides a return force on the linear shaft upon removal of voltage from the single, rolled polymer actuator. The single, rolled polymer actuator may be fixedly connected to the motor housing, and the actuator plate (e.g., the actuator plate 770 illustrated in FIG. 7B) may be connected to an end of the single, rolled polymer actuator. The spring may be connected to an actuator plate and the motor housing such that the spring provides a return spring force upon the actuator plate when voltage is removed from the single, rolled polymer actuator.

Figure 8:
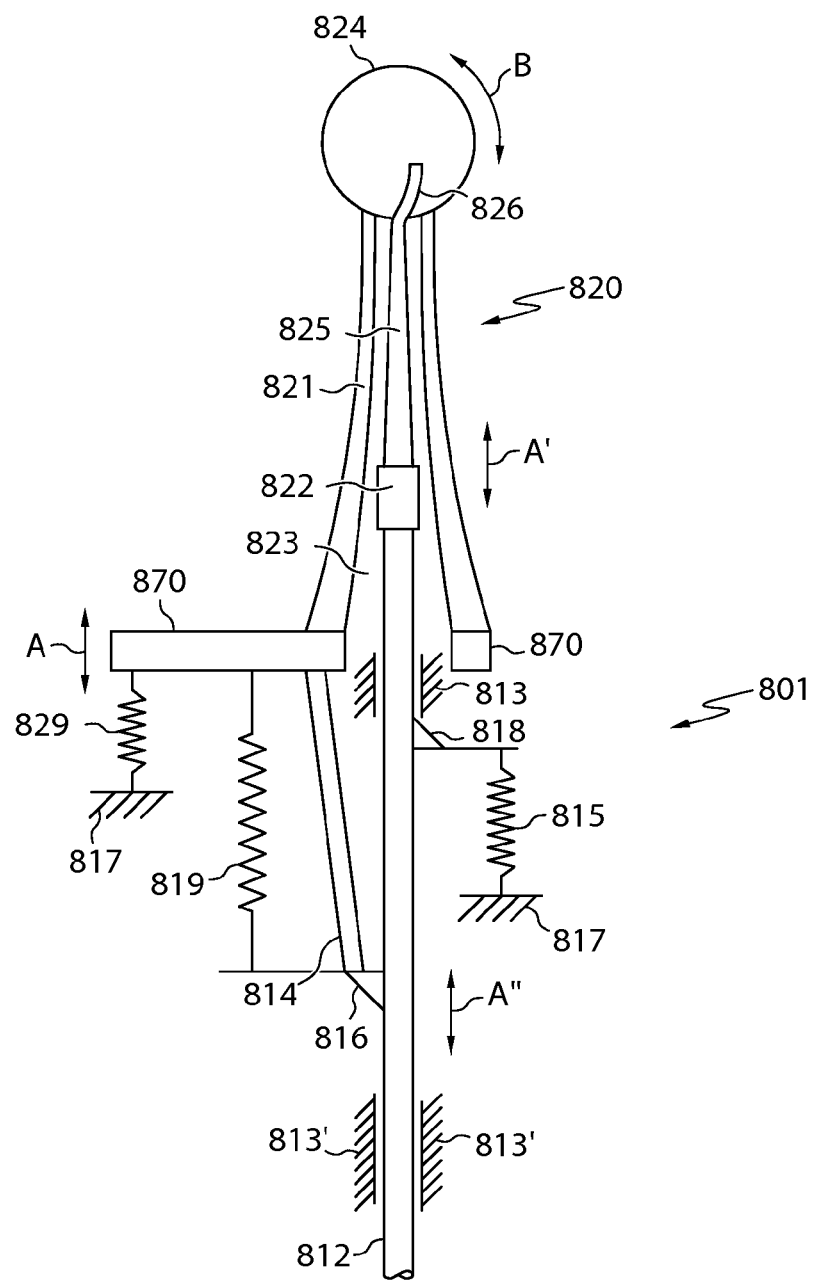
FIG. 8 schematically depicts an exemplary linear electro-polymer motor incorporated into an exemplary toothbrush device according to one or more embodiments described and illustrated herein.

FIG. 8 depicts a schematic illustration of an exemplary linear electro-polymer motor 801 coupled to an adapter 820. In this exemplary embodiment, the linear shaft 812 is connected to an actuator base 870 (rather than the device housing as depicted in FIGS. 1 and 2) by a polymer actuator 814 and a return spring 819. A first end of the polymer actuator 814 is fixedly connected to the linear shaft 812 at an actuator connection region 816, and a second end is fixedly connected to the actuator base 870. The linear shaft 812 may be guided by guide features 813/813' (e.g., guide sleeves or guide springs).

The actuator base 870 may be further coupled to a fixed member 817 (e.g., a device housing) by a first spring 829. The linear shaft 812 may be coupled to the fixed member 817 by a second spring 815. Springs 829 and 815 may allow the actuator base 870 and the linear shaft 812, respectively, to be in a middle/rest position. The second spring 815 may be fixedly coupled to the linear shaft 812 at a spring connection region 818. The actuator base 870 has one degree of freedom in the axial direction, as does the linear shaft 812. The illustrated arrangement allows the actuator base 870 to move relative to the fixed member 817 when the polymer actuator 814 moves the linear shaft 812, thereby providing a vibration control that may reduce or eliminate consumer-noticeable vibration on the device housing. It should be understood that more or fewer springs may be used to couple the various components.

In the embodiment illustrated in FIG. 8, the adapter 820 is coupled to the actuator base 870 rather than the device housing (i.e., the fixed member 817). Therefore, the adaptor 820, the actuator base 870, and the linear shaft 812 may translate as indicated by arrows A, A', and A". The adaptor 820 comprises an adapter housing 821, a push rod 825, a rocker arm 826, a rotating member 824. In one embodiment, the adapter housing 821 may be removably coupled to the actuator base 870 such that it is not in contact with the fixed member 817. A portion of the linear shaft 812 may extend into an adapter cavity 823 defined by the adapter housing 821 and may be removably coupled to the push rod 825 by a coupling feature 822 (e.g., by a snap fit or an interference fit). Movement of the actuator base 870, the linear shaft 812, and the adapter 820 causes the push rod 825 to push the rocker arm 826 to translate periodic linear movement into oscillating angular movement of the rotating member 824, as indicated by arrow B.

In another embodiment, an additional polymer actuator (not shown) may be fixedly connected to the actuator base 870 and the fixed member 817 in parallel with the first spring 829. With this configuration, movement of the linear shaft 812, actuator base 870, and the adapter 820 may be actively controlled and different brushing modes realized with an adapter having a rotating member: 1) only rotational movement of the rotating member 824; 2) only linear movement of the adapter 820; 3) a combination of rotational movement of the rotating member 824 and linear movement of the adapter 820 (i.e., curvilinear movement of the rotating member 824).

Figure 9:
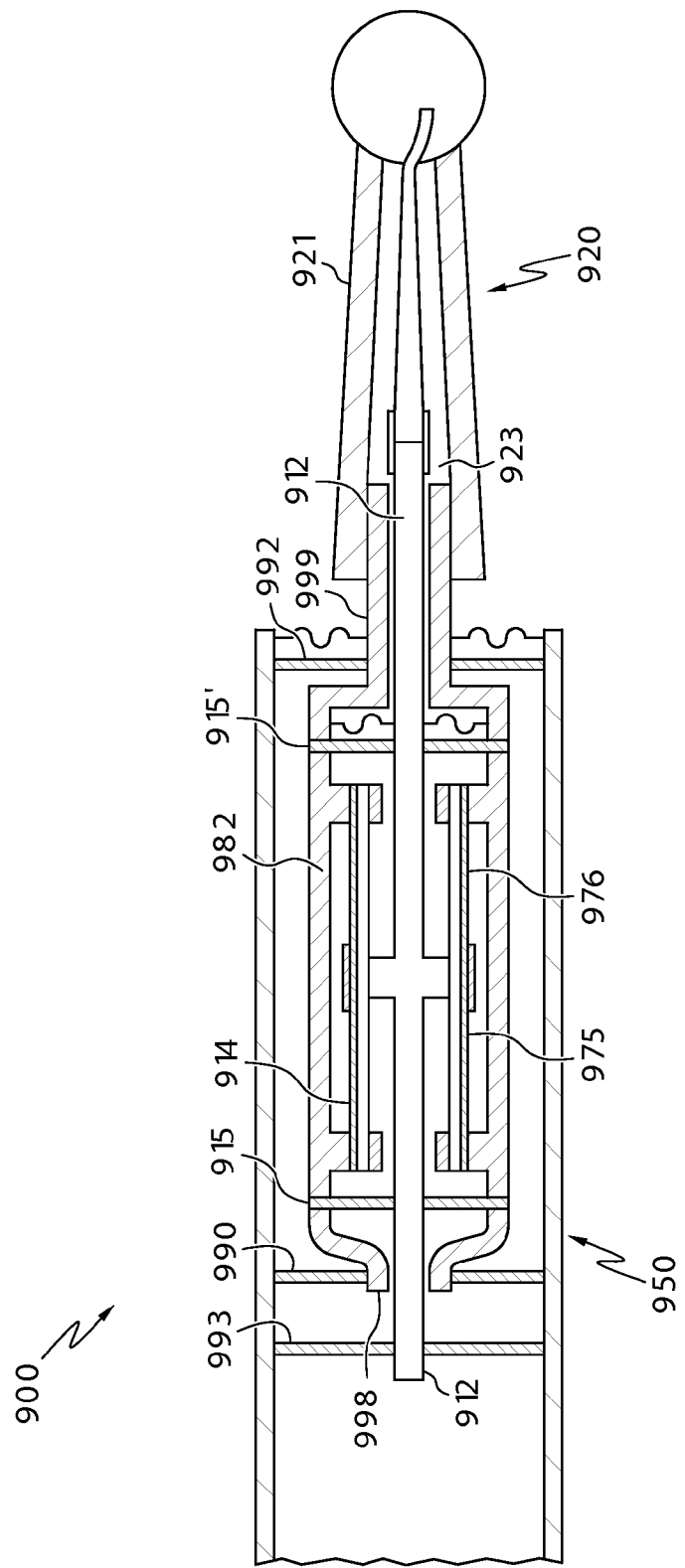
FIG. 9 illustrates a cross-sectional view of an exemplary toothbrush device having an exemplary linear electro-polymer motor according to one or more embodiments described and illustrated herein.

FIG. 9 illustrates one implementation of the linear electropolymer motor 801 having vibration control that is illustrated in FIG. 8. In this embodiment, the device 900 comprises an actuator base that is configured as a motor housing 982 similar to the motor housing 782 illustrated in FIG. 7. The first and second polymer actuators 975, 976 may be configured as a rolled polymer actuator 914 and maintained within the motor housing 982 as illustrated in FIG. 7. Rather than being directly connected to the device housing 950, the motor housing 982 may be indirectly connected to the device housing 950 by a rear end motor housing spring 990 and an adapter end motor housing spring 992. Alternatively, the motor housing 982 may coupled to the device housing 950 by only one motor housing spring (e.g., only the adapter end motor housing spring 992). The linear shaft 912 may be fixedly connected to the first and second springs 915, 915' as described above and illustrated in FIG. 7. Additionally, the linear shaft 912 may be fixedly connected to a shaft guide spring 993 that supports a rear portion of the linear shaft 912 and aids in providing linear movement of the linear shaft 912.

The motor housing 982 comprises a rear end 998 and an adapter end 999, each having a diameter that is smaller than a diameter of the middle region of the motor housing 982. The rear end 998 of the motor housing may be fixedly connected to the rear end motor housing spring 990, which may have a spiral arm and configured as the springs depicted in FIGS. 6A-6C. The perimeter of the rear end motor housing spring 990 may be fixedly connected to the device housing 950. Other configurations that guide the motor housing 982 and enable linear motion may be utilized.

Similarly, the adapter end motor housing spring 992 may be fixedly coupled to the adapter end 999 and to the device housing 950. The adapter end motor housing spring 992 may be configured as the rear end motor housing spring 990, or as a different configuration that may guide the motor housing 982 and enable linear movement of the motor housing 982. One or more additional springs may also be provided between the motor housing 982 and the device housing 950.

As shown in FIG. 9, the adapter end 999 of the motor housing 982 may extend such that it is configured to be removably coupled to the adapter 920 within the adapter recess 923 defined by the adapter housing 921. In this manner, the adapter 920 may be removably coupled to the motor housing 982 rather than the device housing 950, which may reduce consumer-noticeable vibrations in the device 900 because the motor housing 982 has one degree of freedom to move within the device enclosure. The motor housing 982 may have one degree of freedom because it may be flexibly mounted to the device housing 950 via the rear end motor housing spring 990 and the adapter end motor housing spring 992. The shaft guide spring 993 between the linear shaft 912 and the device housing 950 may further minimize vibration at the device housing 950.

In an alternative embodiment, the motor housing 982 may be coupled to the device housing 950 by one or more additional polymer actuators (not shown). The additional polymer actuators may be in addition to, or in lieu of, the rear end motor housing spring 990 and/or the adapter end motor housing spring 992. For example, an additional polymer actuator may be fixedly connected to the device housing 950 at an exterior surface of the motor housing 982. The one or more additional polymer actuators may be configured to enable the different brushing modes describe above with respect to FIG. 8.

Figure 10A:
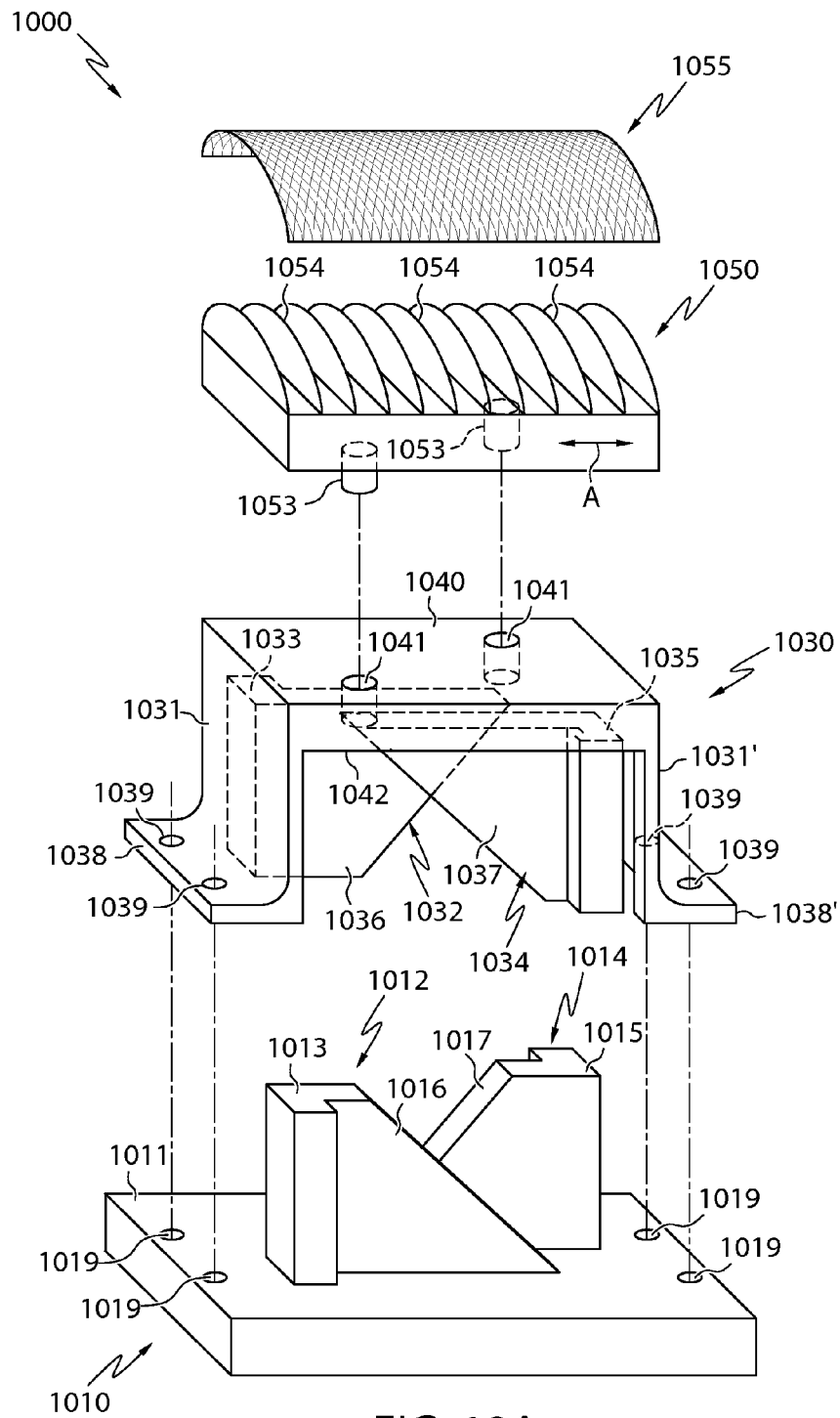
FIG. 10A illustrates an exploded perspective view of an exemplary electric shaver device incorporating exemplary polymer actuators according to one or more embodiments described and illustrated herein.
Figure 10B:
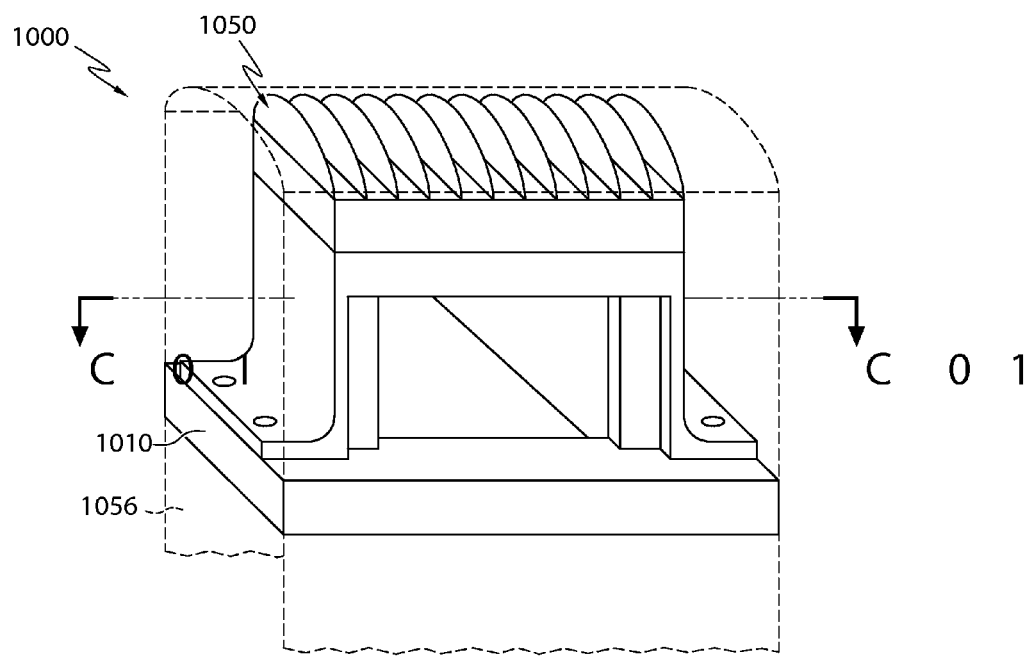
FIG. 10B illustrates an assembled, side perspective view of the exemplary electric shaver device depicted in FIG. 10A.
Figure 10D:
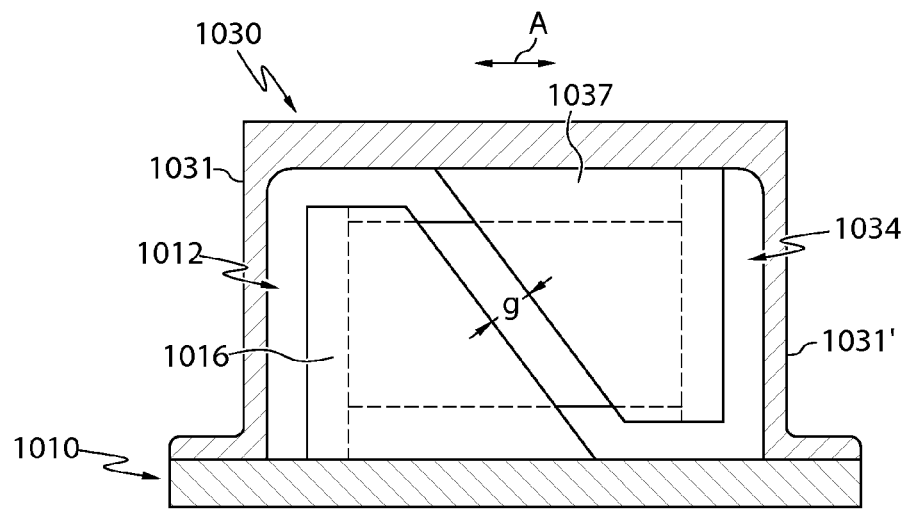
FIG. 10D illustrates a cross-sectional view of the exemplary electric shaver device depicted in FIG. 10C in a first state.
Figure 10E:
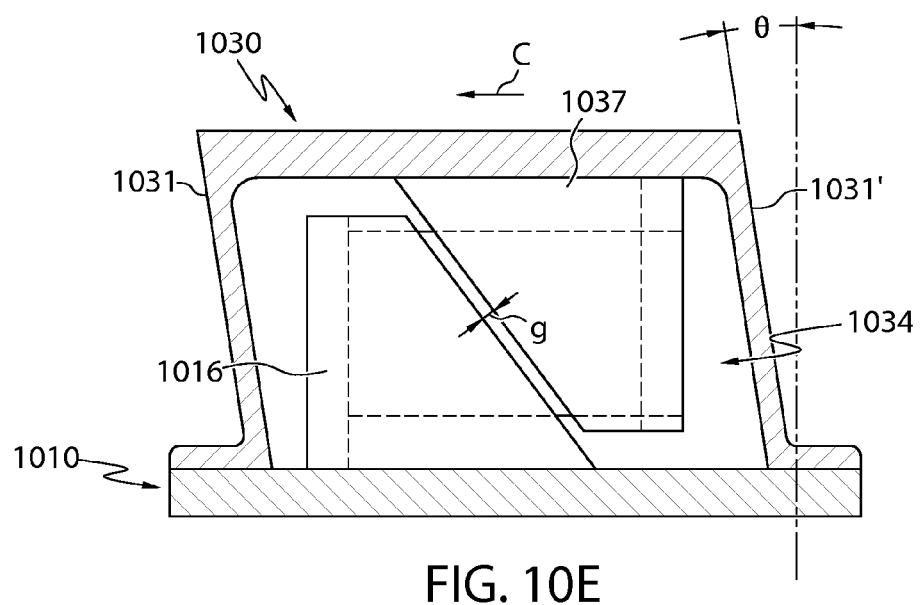
FIG. 10E illustrates a cross-sectional view of the exemplary electric shaver device depicted in FIG. 10C in a second state.

Referring now to FIGS. 10A-10C, an electric shaver device 1000 comprising polymer actuators 1060/1062 is illustrated. FIG. 10A is an exploded, side perspective view of an electric shaver device 1000, FIG. 10B is an assembled, side perspective view of the electric shaver device 1000 illustrated in FIG. 10A, and FIG. 10C is a cross-sectional view of a cross section taken along line A-A of FIG. 10B. FIGS. 10D and 10E are cross-sectional views of a cross section taken along line B-B of FIG. 10C and depict the electric shaver device 1000 in two stages of actuation.

Referring initially to FIG. 10A, the electric shaver device 1000 generally comprises a base 1010, an oscillation bridge 1030, a blade assembly 1050, and a foil cover 1055. The base 1010 generally comprises an upper surface 1011, a first polymer actuator mount 1012, a second polymer actuator mount 1014, and a plurality of fastener holes 1019 for connecting the oscillation bridge 1030 to the base 1010. The base 1010 and the first and second polymer actuator mounts 1012, 1014 may be made of a rigid material, such as metal, plastic, polymers, composites, etc. The base 1010 may be positioned in a first plane.

The first and second polymer actuator mounts 1012, 1014 may extend from the upper surface 1011 of the base 1010 and may comprise an L-shaped engagement region 1013/1015 and a sloping portion 1016/1017. The first polymer actuator mount 1012 may oppose and be offset from the second polymer actuator mount 1014 such that each may be positioned in a separate vertical plane (a first and second vertical plane, respectively). The sloping portion 1016 of the first polymer actuator mount 1012 slopes toward the second polymer actuator mount 1014, and the sloping portion 1017 of the second polymer actuator mount 1014 slopes toward the first polymer actuator mount 1012 (see FIGS. 10D and 10E). The sloping portions may provide increased rigidity to the polymer actuator mounts such that they remain substantially free from bending, while also providing a clearance between opposing polymer actuator mounts during linear translation of the oscillation bridge. It should be understood that geometric configurations other than the illustrated sloping portions may be utilized to provide rigidity to the polymer actuator mounts while also allowing for linear translation of the oscillation bridge.

The oscillation bridge 1030 may comprise an upper surface 1040, a lower surface 1042, a first leaf spring 1031, a second leaf spring 1031', a third polymer actuator mount 1032, and a fourth polymer actuator mount 1034. The oscillation bridge 1030 may further comprise blade assembly connection holes 1041 to couple the blade assembly 1050 to the oscillation bridge 1030. The oscillation bridge 1030 may be located in a second plane that is parallel to the first plane of the base.

The first and second leaf springs 1031, 1031' extend downward from the upper surface 1040 and terminate in a connection flange 1038/1038' having holes 1039 such that the first and second leaf springs 1031, 1031' may be connected to the base with fasteners (e.g., screws). It should be understood that the first and second leaf springs 1031, 1031' may be fixedly connected to the base by other coupling means, such as welding, tacking, soldering, adhesive, etc. The first and second leaf springs 1031, 1031' may be made of a compliant material such that they may move back and forth along the direction indicated by arrow A.

The third and fourth polymer actuator mounts 1032, 1034 extend from the lower surface 1042 of the oscillation bridge 1030. As shown in FIG. 10A, the third and fourth polymer actuator mounts 1032, 1034 may be generally L-shaped in cross section and have engagement regions 1033/1035. Like the first and second polymer actuator mounts 1012, 1014, the third and fourth polymer actuator mounts 1032, 1034 have a sloping portion 1036/1037. The sloping portion 1036 of the third polymer actuator mount 1032 slopes toward the fourth polymer actuator mount 1034, and the sloping portion 1037 of the fourth polymer actuator mount 1034 slopes toward the third polymer actuator mount 1032. When the electric razor is in an assembled state as illustrated in FIG. 10B, the fourth polymer actuator mount 1034 is opposite from the first polymer actuator mount 1012 in the first vertical plane, and the third polymer actuator mount 1032 is opposite from the second polymer actuator mount 1014. The base 1010, oscillation bridge 1030, and blade assembly 1050 may be maintained within a device housing 1056.

The blade assembly 1050 may comprise a plurality of blades 1054 at an upper surface and coupling pins 1053 at a lower surface that may be inserted and secured to the blade assembly connection holes 1041 such that the blade assembly 1050 is fixedly connected to the oscillation bridge 1030. The foil cover 1055 may be secured to the device housing to limit the exposure of the blades 1054.

Referring now to FIG. 10C, a first polymer actuator 1060 is fixedly connected to the first polymer actuator mount 1012 at engagement region 1013 and to the fourth polymer actuator mount 1034 at engagement region 1035. A second polymer actuator 1062 is fixedly connected to the second polymer actuator mount 1014 at engagement region 1015 and to the third polymer actuator mount 1032 at engagement region 1033. The first and second polymer actuators 1060, 1062 may be positioned in parallel to one another such that each pull (or push) in different directions when activated. By alternating voltage that is applied to the first and second polymer actuators 1060, 1062, the first and second polymer actuators 1060, 1062 may be controlled to move the oscillation bridge 1030 about a nearly linear, limited travel range, as indicated by arrow A. By rocking the oscillation bridge 1030, the blade assembly 1050 may travel back and forth to move the blades 1054 across a user's skin.

FIG. 10D illustrates a cross-sectional view of the cross section line B-B of FIG. 10C. FIG. 10D illustrates the oscillation bridge 1030 at rest with respect to the base 1010. The first and second polymer actuators 1060 and 1062 do not have voltage applied thereto at this position. In the embodiment illustrated in FIG. 10D, gap g is present between the sloping portion 1016 of the first polymer actuator mount 1012 and the sloping portion 1037 of the fourth polymer actuator mount 1034. The clearance provided by the gap g may allow for reciprocating linear movement of the oscillation bridge 1030 along a single dimension, as indicated by arrow A.

FIG. 10E also illustrates a cross-sectional view of the cross section line B-B of FIG. 10C, wherein the oscillation bridge 1030 has linearly translated with respect to the base 1010 as indicated by arrow C. The oscillation bridge 1030 has linearly translated due to application of voltage to the electrodes of the first polymer actuator 1060. The first polymer actuator 1060 has expanded due to the applied voltage, thereby moving the fourth polymer actuator mount 1034 closer to the first polymer actuator mount 1012 and making the gap g' illustrated in FIG. 10E smaller than the gap g illustrated in FIG. 10D. Accordingly, the sloping portions 1016, 1017, 1036, 1037 of the polymer actuator mounts 1012, 1014, 1032, 1034 may allow maximum outreach and movability of the oscillation bridge 1030.

As used herein, the term "contact elements" is used to refer to any suitable element which can be inserted into the oral cavity. Some suitable elements include bristle tufts, elastomeric massage elements, elastomeric cleaning elements, massage elements, tongue cleaners, soft tissue cleaners, hard surface cleaners, abrasive elastomeric elements, elastomeric elements in a particular orientation or arrangement, e.g. pivoting fins, prophy cups, combinations thereof, or the like. Exemplary suitable contact elements are disclosed in U.S. Pat. App. Pub. Nos. 2002/0059685; 2005/0000043; 2004/0177462; 2005/0060822; 2004/0154112; 2008/0178401; 2009/0007357; U.S. Pat. Nos. 6,151,745; 6,058,541; 6,041,467; 6,553,604; 6,564,416; 6,826,797; 6,993,804; 6,453,497; 6,993,804; 6,041,467, all of which are herein incorporated by reference in their entirety. Additional suitable examples of elastomeric cleaning elements and/or massaging elements are described in U.S. Patent Application Publication Nos. 2007/0251040; 2004/0154112; 2006/0272112; and in U.S. Pat. Nos. 6,553,604; 6,151,745. The cleaning elements may be tapered, notched, crimped, dimpled, or the like. Some suitable examples of these cleaning elements and/or massaging elements are described in U.S. Pat. Nos. 6,151,745; 6,058,541; 5,268,005; 5,313,909; 4,802,255; 6,018,840; 5,836,769; 5,722,106; 6,475,553; and U.S. Patent Application Publication No. 2006/0080794.

The contact elements may be attached to the head in any suitable manner. Conventional methods include stapling, anchor free tufting, and injection mold tufting. For those contact elements that comprise an elastomer, these elements may be formed integral with one another, e.g. having an integral base portion and extending outward therefrom.

The head may comprise a soft tissue cleanser constructed of any suitable material. Some examples of suitable material include elastomeric materials; polypropylene, polyethylene, etc; the like, and/or combinations thereof. The soft tissue cleanser may comprise any suitable soft tissue cleansing elements. Some examples of such elements as well as configurations of soft tissues cleansers on a toothbrush are described in U.S. Patent Application Nos. 2006/0010628; 2005/0166344; 2005/0210612; 2006/0195995; 2008/0189888; 2006/0052806; 2004/0255416; 2005/0000049; 2005/0038461; 2004/0134007; 2006/0026784; 20070049956; 2008/0244849; 2005/0000043; 2007/140959; and U.S. Pat. Nos. 5,980,542; 6,402,768; and 6,102,923.

For those embodiments which include an elastomeric element on a first side of the head and an elastomeric element on a second side of the head (opposite the first), the elastomeric elements may be integrally formed via channels or gaps which extend through the material of the head. These channels or gaps can allow elastomeric material to flow through the head during an injection molding process such that both the elastomeric elements of the first side and the second side may be formed in one injection molding step.

It should now be understood that embodiments described herein may enable movement of a linear shaft or other similar structure in a linear direction by the use of linear electro-polymer motors. Such linear electro-polymer motors may be utilized as a linear drive system in small appliance devices, such as toothbrushes, electric razors, tongue cleaners, and the like. Embodiments described herein may reduce the complexity of existing linear drive systems currently implemented in such small appliance devices because polymer actuators utilized in the linear electro-polymer motors described herein may have fewer moving parts than traditional linear drive systems.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be understood to those skilled in the art that various other changes and modifications can be made without departing from the spirit and scope of the invention. It is therefore intended to cover in the appended claims all such changes and modifications that are within the scope of this invention.

What is claimed is:

1. A linear electro-polymer motor comprising:
   a fixed member;
   a linear shaft having an axis associated therewith;
   a polymer actuator comprising a first end and a second end, wherein the first end of the polymer actuator is fixedly connected to the linear shaft and the second end of the polymer actuator is fixedly connected to the fixed member; and
   a bias member comprising a first end and a second end, wherein:
      the first end of the bias member is fixedly connected to the linear shaft;
      the second end of the bias member is fixedly connected to the fixed member such that a spring force provided by the bias member opposes a movement of the linear shaft provided by the polymer actuator; and
      the polymer actuator changes length after receipt of voltage to move the linear shaft along the axis,
      wherein the bias member comprises a second polymer actuator.

2. The linear electro-polymer motor of claim 1, wherein the bias member comprises a spring.

3. The linear electro-polymer motor of claim 1, further comprising a guiding sleeve, wherein the linear shaft is positioned through the guiding sleeve such that the movement of the linear shaft is substantially linear.

4. A device comprising:
   a device housing defining a device enclosure therein; and
   a linear electro-polymer motor at least partially positioned within the device enclosure defined by the device housing, the linear electro-polymer motor comprising:
      a linear shaft having an axis associated therewith;
      a polymer actuator comprising a first end and a second end, wherein the first end of the polymer actuator is fixedly connected to the linear shaft and the second end of the polymer actuator is fixedly connected to the device housing within the device enclosure; and
      a bias member comprising a first end and a second end, wherein:
         the first end of the bias member is fixedly connected to the linear shaft;
         the second end of the bias member is fixedly connected to the device housing such that a spring force provided by the bias member opposes a movement of the linear shaft provided by the polymer actuator; and
         the polymer actuator changes length after receipt of voltage to move the linear shaft along the axis,
         wherein the linear shaft comprises an actuator protrusion and the polymer actuator is fixedly connected to the actuator protrusion and the bias member comprises a first flat spring and a second flat spring.

5. The device of claim 4, wherein the linear shaft at least partially extends out of the device enclosure defined by the device housing.

6. The device of claim 4, wherein the device is an electric toothbrush.

7. The device of claim 4, further comprising an adapter removably coupled to the linear shaft, wherein linear movement of the linear shaft moves the adapter along the axis of the linear shaft.

8. The device of claim 4, wherein:
   the first and second flat springs each comprise a first end, and two outer arms and a middle arm extending from the first end;
   a lower portion of the two outer arms are fixedly connected to the support wall of the chassis;
   the middle arm is not fixedly connected to the device housing such that the middle arm acts as a cantilever spring portion; and
   the linear shaft is fixedly connected to the middle arm of the first and second flat springs.

9. The device of claim 4, further comprising:
   a chassis comprising a support wall, a first side wall, and a second side wall, wherein the chassis is fixedly connected to the device housing within the device enclosure;
   a first actuator coupling plate and a second actuator coupling plate, wherein the linear shaft is fixedly positioned through the first actuator coupling plate and the second actuator coupling plate; and
   a second polymer actuator comprising a first end and a second end, wherein the first end is fixedly connected to the second actuator coupling plate and the second end is fixedly connected to the second side wall of the chassis, wherein:
      the first end of the polymer actuator is fixedly connected to the first actuator coupling plate and the second end of the polymer actuator is fixedly connected to the first side wall of the chassis;

the bias member comprises a first flat spring and a second flat spring; and the first and second flat springs flexibly couple the linear shaft to the chassis.

10. The device of claim 9, wherein:

the first and second flat springs each comprise a first end, and two outer arms and a middle arm extending from the first end;

a lower portion of the two outer arms are fixedly connected to the support wall of the chassis;

the middle arm is not fixedly connected to the device housing such that the middle arm acts as a cantilever spring portion; and the linear shaft is fixedly connected to the middle arm of the first and second flat springs.

11. The device of claim 9, wherein the first actuator coupling plate, the second actuator coupling plate, the first flat spring, and the second flat spring are orientated normal to the axis of the linear shaft.

12. A device comprising:

a device housing defining a device enclosure therein; and a linear electro-polymer motor at least partially positioned within the device enclosure defined by the device housing, the linear electro-polymer motor comprising:

an actuator base coupled to the device housing within the device enclosure by an actuator spring;

a linear shaft having an axis associated therewith;

a polymer actuator comprising a first end and a second end, wherein the first end of the polymer actuator is fixedly connected to the linear shaft and the second end of the polymer actuator is fixedly connected to the actuator base;

a return spring having a first end fixedly connected to the actuator base and a second end fixedly connected to the linear shaft; and a bias member comprising a first end and a second end, wherein:

the first end of the bias member is fixedly connected to the linear shaft;

the second end of the bias member is fixedly connected to the device housing; and the polymer actuator changes length after receipt of a voltage, wherein the device further includes an adapter comprising a first end, a second end, a recess extending between the first end and the second end, a push rod coupled to the linear shaft at a first end of the push rod, and a rotating member, wherein the rotating member is coupled to the push rod at a second end of the push rod, linear movement of the linear shaft oscillates the rotating member about a rotational axis, and the second end of the adapter is removably coupled to the actuator base such that application of voltage to the polymer actuator linearly moves the adapter and the linear shaft with respect to the device housing.

13. The device of claim 12, wherein the device is an electric toothbrush.

14. A device comprising:

a base located in a first plane;

an oscillation bridge flexibly coupled to the base and located in a second plane parallel to the first plane; and a polymer actuator comprising a first end and a second end, wherein the first end of the polymer actuator is coupled to the base and a second end of the polymer actuator is coupled to the oscillation bridge, and a voltage applied to the polymer actuator translates the oscillation bridge with respect to the base such that the oscillation bridge linearly travels within the second plane, wherein the base comprises an upper surface, a first polymer actuator mount extending from the upper surface, and a second polymer actuator mount extending from the upper surface, wherein the first polymer actuator mount is in a first vertical plane and the second polymer actuator mount is in a second vertical plane, the oscillation bridge comprises an upper surface, a first end, a second end, a lower surface, a first leaf spring extending from the first end of the oscillation bridge and fixedly connected to the upper surface of the base, a second leaf spring extending from the second end of the oscillation bridge and fixedly connected to the upper surface of the base, a third polymer actuator mount extending from the lower surface and located in the first vertical plane, the third polymer actuator mount is opposite from the second polymer actuator mount, and a fourth polymer actuator mount extending from the lower surface and located in the second vertical plane, wherein the fourth polymer actuator mount is opposite from the first polymer actuator mount;

wherein the polymer actuator further comprises a first polymer actuator comprising a first end and a second end, wherein the first end is fixedly connected to the first polymer actuator mount and the second end is fixedly connected to the fourth polymer actuator mount; and a second polymer actuator comprising a first end and a second end, wherein the first end is fixedly connected to the second polymer actuator mount and the second end is fixedly connected to the third polymer actuator mount; and an alternating voltage applied to the first polymer actuator and the second polymer actuator causes the oscillation bridge to linearly translate in the second plane.

15. The device of claim 14, further comprising a blade assembly comprising a plurality of blades, the blade assembly fixedly coupled to the upper surface of the oscillation bridge.

* * * * *